US 7,729,529 B2

(12) United States Patent
Wu et al.

(10) Patent No.: US 7,729,529 B2
(45) Date of Patent: Jun. 1, 2010

(54) COMPUTER-IMPLEMENTED METHODS FOR DETECTING AND/OR SORTING DEFECTS IN A DESIGN PATTERN OF A RETICLE

(75) Inventors: Kenong Wu, Davis, CA (US); David Randall, Sunnyvale, CA (US); Kourosh Nafisi, Los Altos, CA (US); Ramon Ynzunza, Milpitas, CA (US); Ingrid B. Peterson, Menlo Park, CA (US); Ariel Tribble, Fremont, CA (US); Michal Kowalski, Santa Cruz, CA (US); Lisheng Gao, Morgan Hill, CA (US); Ashok Kulkarni, San Jose, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 1160 days.

(21) Appl. No.: 11/005,658

(22) Filed: Dec. 7, 2004

(65) Prior Publication Data

US 2006/0291714 A1 Dec. 28, 2006

(51) Int. Cl.
*G06K 9/00* (2006.01)
*H01L 21/66* (2006.01)
*G06F 17/50* (2006.01)
(52) U.S. Cl. .................. 382/149; 382/144; 382/145; 382/147; 382/148; 438/15; 716/1; 716/21
(58) Field of Classification Search .................. 382/149
See application file for complete search history.

(56) References Cited

U.S. PATENT DOCUMENTS

| 4,347,001 | A | * | 8/1982 | Levy et al. ................. 356/398 |
| 5,544,256 | A | * | 8/1996 | Brecher et al. .............. 382/149 |
| 5,694,478 | A | * | 12/1997 | Braier et al. ................ 382/133 |
| 5,965,306 | A | * | 10/1999 | Mansfield et al. ............ 430/22 |
| 5,991,699 | A | * | 11/1999 | Kulkarni et al. ............... 702/83 |
| 6,097,887 | A | * | 8/2000 | Hardikar et al. ............. 717/105 |

(Continued)

OTHER PUBLICATIONS

Identifying Process Window Marginalities of Reticle Designs for 0.15/0.13 um Technologies, Lo et al., Photomask and Next-Generation Lithography Mask Technology, SPIE vol. 5130, 2003, p. 829-837.*

(Continued)

*Primary Examiner*—Vikkram Bali
*Assistant Examiner*—Michelle Entezari
(74) *Attorney, Agent, or Firm*—Ann Marie Mewherter

(57) ABSTRACT

Various computer-implemented methods are provided. One method for sorting defects in a design pattern of a reticle includes searching for defects of interest in inspection data using priority information associated with individual defects in combination with one or more characteristics of a region proximate the individual defects. The priority information corresponds to modulation levels associated with the individual defects. The inspection data is generated by comparing images of the reticle generated for different values of a lithographic variable. The images include at least one reference image and at least one modulated image. A composite reference image can be generated from two or more reference images. The method also includes assigning one or more identifiers to the defects of interest. The identifier(s) may include, for example, a defect classification and/or an indicator identifying if the defects of interest are to be used for further processing.

19 Claims, 9 Drawing Sheets

U.S. PATENT DOCUMENTS

| | | | |
|---|---|---|---|
| 6,233,719 B1 * | 5/2001 | Hardikar et al. ................ 716/1 |
| 6,268,093 B1 | 7/2001 | Kenan et al. |
| 6,292,582 B1 * | 9/2001 | Lin et al. .................... 382/149 |
| 6,327,033 B1 | 12/2001 | Ferguson et al. |
| 6,513,151 B1 * | 1/2003 | Erhardt et al. ................ 716/21 |
| 6,535,628 B2 * | 3/2003 | Smargiassi et al. .......... 382/149 |
| 6,803,554 B2 | 10/2004 | Ye et al. |
| 6,807,503 B2 | 10/2004 | Ye et al. |
| 6,873,720 B2 * | 3/2005 | Cai et al. .................... 382/149 |
| 6,919,957 B2 * | 7/2005 | Nikoonahad et al. ..... 356/237.2 |
| 6,983,060 B1 * | 1/2006 | Martinent-Catalot et al. .......................... 382/100 |
| 7,001,697 B2 * | 2/2006 | Park et al. ..................... 430/5 |
| 7,107,571 B2 * | 9/2006 | Chang et al. .................. 716/19 |
| 7,304,721 B2 * | 12/2007 | Haffner et al. ................ 356/72 |
| 7,386,839 B1 * | 6/2008 | Golender et al. ............ 717/131 |
| 2001/0043735 A1 * | 11/2001 | Smargiassi et al. .......... 382/149 |
| 2002/0035461 A1 * | 3/2002 | Chang et al. .................. 703/13 |
| 2002/0164065 A1 | 11/2002 | Cai et al. |
| 2002/0186878 A1 * | 12/2002 | Hoon et al. .................. 382/149 |
| 2002/0186879 A1 | 12/2002 | Hemar et al. |
| 2003/0098805 A1 * | 5/2003 | Bizjak ........................ 341/139 |
| 2003/0138138 A1 * | 7/2003 | Vacca et al. .................. 382/145 |
| 2003/0169916 A1 * | 9/2003 | Hayashi et al. ............. 382/145 |
| 2003/0226951 A1 | 12/2003 | Ye et al. |
| 2003/0237064 A1 * | 12/2003 | White et al. .................... 716/5 |
| 2004/0032908 A1 * | 2/2004 | Hagai et al. ............. 375/240.25 |
| 2004/0091142 A1 * | 5/2004 | Peterson et al. ............. 382/144 |
| 2004/0228515 A1 * | 11/2004 | Okabe et al. ................ 382/145 |
| 2004/0243320 A1 * | 12/2004 | Chang et al. ................... 702/30 |
| 2005/0008218 A1 * | 1/2005 | O'Dell et al. ............... 382/145 |
| 2005/0062962 A1 * | 3/2005 | Fairley et al. ............. 356/237.2 |
| 2006/0082763 A1 * | 4/2006 | Teh et al. ...................... 356/72 |
| 2006/0159333 A1 * | 7/2006 | Ishikawa .................... 382/149 |
| 2006/0193506 A1 * | 8/2006 | Dorphan et al. ............. 382/145 |
| 2006/0193507 A1 * | 8/2006 | Sali et al. .................... 382/145 |
| 2006/0265145 A1 * | 11/2006 | Huet et al. .................... 702/35 |
| 2007/0035728 A1 * | 2/2007 | Kekare et al. ............ 356/237.5 |
| 2008/0049994 A1 * | 2/2008 | Rognin et al. ............... 382/128 |

OTHER PUBLICATIONS

International Search Report, PCT/US2005/044695 mailed May 22, 2006.

* cited by examiner

COMPUTER-IMPLEMENTED METHODS FOR DETECTING AND/OR SORTING DEFECTS IN A DESIGN PATTERN OF A RETICLE

BACKGROUND OF THE INVENTION

1. Field of the Invention

The present invention generally relates to computer-implemented methods for detecting and/or sorting defects in a design pattern of a reticle. Certain embodiments relate to a computer-implemented method that includes generating a composite reference image from two or more reference images and using the composite reference image for comparison with other sample images for defect detection. Other embodiments include sorting defects using priorities, defect attributes, defect appearance and background information. Additional embodiments relate to assisting the user in locating the relevant and unique defects based on background appearance and other characteristics combined with wafer design data and knowledge of process modulation.

2. Description of the Related Art

The following description and examples are not admitted to be prior art by virtue of their inclusion in this section.

The rapid decrease in $k_1$ (line-width=$k_1$ ($\lambda$/NA)) in lithographic manufacture of semiconductor devices has necessitated the use of Resolution Enhancement Techniques (RET). These RET include, but are not limited to, Optical Proximity Corrections (OPC), Phase Shift Masks (PSM), and assist bar corrections. Although they are implemented in semiconductor device designs to facilitate low $k_1$ lithography, these RET make reticles more difficult and consequently more expensive to manufacture.

Semiconductor device design and reticle manufacturing quality are verified by different procedures before the reticle enters a semiconductor fabrication facility to begin production of integrated circuits. The semiconductor device design is checked by software simulation to verify that all features print correctly after lithography in manufacturing. Such checking is commonly referred to as "Design Rule Checking." The output of this design rule checking can produce a potentially large set of critical points, sometimes referred to as "hot spots" on the reticle layout. This set can be used to direct a point-to-point inspector, such as at a Review SEM, but this can be highly inefficient due to the number of critical points. The reticle is inspected at the mask shop for reticle defects and measured to ensure that the features are within specification. Marginal RET designs not noted by simulation checks translate into electrical failures in wafer fabrication, affect yield, and possibly remain unnoticed until wafer fabrication is complete.

Traditional methods employed in the inspection of complex mask patterns place tremendous demand on reticle inspection tools. One technique for performing image qualification entails using focus exposure matrix techniques. Performing an inspection of a conventional focus exposure matrix introduces a complication in that every exposure field is different. Die-to-die comparison is performed between adjacent local exposure fields. Any pattern change that may occur at a defocus position that is physically located farther than one exposure field from the nominal exposure field will not, therefore, be detected as different because the nominal exposure field is no longer factored in the comparison. Moreover, current reticle inspection techniques cannot detect the presence of an error in the design database. Prior art single die reticle inspection entails implementation of a design simulation technique in which a signal derived from an actual reticle is subtracted from a simulated design reference.

What is needed, therefore, is an inspection technique that is effective in locating pattern anomalies in a single die or a multi-die reticle and detecting reticle design errors resulting from errors in the design data base.

Methods have been invented to address the above-described needs. These methods are often referred to as "Process Window Qualification" Methods or "PWQ" Methods and are described in U.S. Patent Application Publication No. US2004/0091142 to Peterson et al., which is incorporated by reference as if fully set forth herein. Software packages that are configured to perform methods such as those described by Peterson et al. are commercially available from KLA-Tencor, San Jose, Calif. In general, the methods can be used to find design elements of a reticle that will fail in lithographic processing when used with lithographic variables (e.g., focus, dose, etc.) that are within a normal process window for the reticle.

PWQ methods are often performed using wafer inspection tools such as any of the wafer inspection tools that are commercially available from KLA-Tencor. In one example, a wafer is printed with columns of dies, each containing the design pattern on the reticle, in an N-M-N pattern. The "N" dies are those dies that are printed with a "nominal" lithographic variable (which may also be commonly referred to as a "nominal lithography parameter," a "nominal lithographic process parameter," or a "nominal process condition"). The "M" dies are printed with a value of the lithographic variable that is different than the nominal lithographic variable. In other words, the M dies are printed with a modulated lithographic variable. The nominal lithographic parameter may be the value of the lithographic parameter known to represent the "best condition" for exposure of a wafer with the reticle. Alternatively, the nominal lithographic parameter may be assigned a different baseline value of the lithographic parameter. The lithographic variable can be modulated positively and negatively with respect to the nominal lithographic variable in rows of dies printed on the wafer.

After exposure of the wafer with the reticle, the wafer is inspected by comparing the modulated die to the two nominal dies on either side of the modulated die. Adjacent dies are compared after both of the adjacent dies have been imaged. Therefore, the comparison is performed sequentially in the order in which the dies are imaged. Differences between the adjacent dies can be stored as potential defects.

Positively modulated dies and negatively modulated dies may be handled separately for purposes of analysis. In addition, the defects that are detected in the modulated dies may be analyzed to determine the priority or relevance of the defects. Furthermore, the user may be able to review the defects to find the critical or important defects that were detected.

Although the above-described PWQ methods have proved successful in meeting the needs outlined above, these methods can also be improved. For example, in the inspection process, the modulated dies are compared to exactly two nominal or reference dies. Randomly occurring defects in either or both of the reference dies may adversely affect the results if they result in reducing the priority of defects in the modulated dies. In addition, using a three die comparison (i.e., two reference dies for each modulated die) results in the use of most of the wafer area for printing the reference dies.

In the PWQ software used today, potential failure points in the design pattern are identified by looking for repeating defects. Unfortunately, by its very nature, the experiment can produce an overwhelming number of unimportant repeating defects, particularly in the dies that are highly modulated. Automatic defect classification (ADC) is one way to reduce the number of candidate defects. However, the inline ADC (iADC) method that is available for PWQ uses additional information about the defect itself, and much of this information is irrelevant to finding the most likely failure points. A newer version of the iADC method as described in U.S. patent application Ser. No. 10/954,968 to Huet et al., which is incorporated by reference as if fully set forth herein, provides the capability of focusing on background features. However, in these methods, a user selects background features from the complete set of available features that are used to classify defects thereby creating an extra step in the setup of the inspection. Additionally, in current methods for reviewing defects, it is difficult to obtain multiple examples of potentially interesting defects.

The PWQ methods may also be altered to use a stored "golden die" image for comparison to the modulated images. A "golden die" image may be generally defined as an image of design pattern information on a reticle that is known in some manner to be free of defects. Therefore, by using a golden die image, the number of nominal reference dies printed on the wafer may be reduced, or even eliminated, thereby allowing more modulated dies to be printed on the wafer. However, there are disadvantages to using such a golden die image. For example, a detailed golden die image can require hundreds of Gbytes of storage. On the other hand, the detail of the golden die image may be reduced, but compromising on the detail of the golden die image compromises the effectiveness of the inspection method. Furthermore, a golden die image most likely is not formed under the same processing conditions as the test die, particularly if the golden die image is generated by simulation or if the golden die image was obtained from a different wafer than the wafer on which the modulated dies are printed. The differences in formation of the golden die and the modulated dies may result in false defect detection during inspection of the modulated dies. Moreover, reading the golden image from storage media can be slower that reacquiring the golden image from an image computer or another computer system.

Accordingly, it may be advantageous to develop computer-implemented methods for detecting and/or sorting defects in a design pattern of a reticle that allows accurate defect detection while using relatively few nominal reference dies, increases the accuracy of the defect detection by reducing the adverse effects of defects in the nominal reference dies on the accuracy of the defect detection, allows rapid identification and removal of unimportant repeating defects so that these defects do not obscure the defects of interest, allows multiple examples of interesting defects to be found relatively easily, allows classification of defects in a substantially automated manner, or achieves one or more of the above improvements without using a stored golden die image of the design pattern on the reticle.

SUMMARY OF THE INVENTION

One embodiment relates to a computer-implemented method for sorting defects in a design pattern of a reticle. The method includes searching for defects of interest in inspection data using priority information and defect attributes associated with individual defects in combination with one or more characteristics of a region proximate the individual defects and one or more characteristics of defects. The inspection data is generated by comparing images of the reticle generated for different values of a lithographic variable. The images include at least one reference image and at least one modulated image. The method also includes assigning one or more identifiers to the defects of interest.

In one embodiment, the priority information is derived from the relationship between inspected defects and their corresponding modulation levels. In another embodiment, defect attributes contain simple defect information such as location, size, intensity magnitude and polarity as well as inspection parameters. Defects are filtered by defect priorities and attributes. The filtering criteria can be selected by user. In some embodiments, the one or more characteristics of regions proximate the defects and on the defects are computed from reference and defect images, respectively.

In another embodiment, the method may include grouping the defects of interest based on the one or more characteristics of the region proximate the individual defects or the one or more characteristics of the defects, or a combination thereof. The characteristics used in grouping are selected by the user. In a different embodiment, the method may include retrieving defects which are similar to given defects based on defect appearance, attributes and one or more characteristics of region proximate the defects. The retrieving criteria can be selected by the user.

In one embodiment, the one or more identifiers may include a defect classification. In another embodiment, the one or more identifiers may include an indicator identifying if the defects of interest are to be used for further processing. In one such embodiment, assigning the one or more identifiers is performed automatically based on the priority information and defect classification.

In an additional embodiment, the method may include comparing the potential defects of interest to the results generated by design rule checking performed on design pattern data of the reticle to determine if the defects of interest correlate to design rule checking critical points. In one such embodiment, the method may also include removing from the inspection data the defects that do not correlate with the critical points. In a similar manner, the method may include comparing the potential defects of interest to the results generated by optical rule checking (ORC) performed on design pattern data of the reticle. In general, steps described herein involving the use of DRC results may alternatively be performed using ORC results. Each of the embodiments of the method described above may include any other step(s) described herein.

Another embodiment of the invention relates to a computer-implemented method for detecting defects in a design pattern of a reticle. The method includes acquiring images of the reticle for different values of a lithographic variable. The images include two or more reference images obtained at nominal values and one or more modulated images. The method also includes generating a composite reference image from the two or more reference images. In addition, the method includes comparing at least two of the images. The at least two of the images include the composite reference image. In one embodiment, the user, with knowledge of the wafer layout or dies printed on the wafer, informs the system which images will be used for reference (e.g., composite or non-composite) and for comparison. In this manner, the user may select the images that are used for comparison. The method further includes determining if a defect is present in the design pattern of the reticle using results of the comparison.

In some embodiments, the one or more characteristics of the region may be selected by a user. In another embodiment, simulated images, as from GDS or simulated aerial images, are used to determine the characteristic(s) of the background, based on the location of the defect in the reticle. The characteristic(s) of the region may be extracted from such images using any technique known in the art. In addition, experimentally generated aerial images may be used in a similar manner. In a different embodiment, high resolution images of the reticle may be used to determine characteristic(s) of the background region proximate the defect, based on the location of the defect in the reticle. A high resolution image of the reticle may be obtained using any appropriate high resolution imaging system known in the art. For example, several commercially available reticle inspection systems are configured to form high resolution images of the reticle.

In addition or alternatively, the critical points may be regrouped or filtered using the "Defects Like Me" function described herein to reduce the population. In this manner, inspecting, measuring, and/or reviewing critical points that are similar may be identified or eliminated.

In addition, the critical points identified by the DRC may be overlaid with the inspection data generated as described herein. The inspection data may be data generated by imaging a wafer on which one or more modulated dies and one or more reference dies are printed. Alternatively, the inspection data may include aerial images of the reticle design pattern generated by simulation or experimentation. In this manner, the defects of interest found as described herein may be compared to inspection data generated by design rule checking to determine if the defects of interest correlate to design rule checking defects. The design rule checking defects that do not correlate with the defects of interest may then be removed from the design rule checking inspection data. In a similar manner, the defects of interest may be compared to data generated by optical rule checking to determine if the defects of interest correlate to optical rule checking defects.

In a further embodiment, the images may include images of an entire swath of dies printed on a wafer using the reticle. In this embodiment, the at least two images used for the comparison may include images of all of the dies in the entire swath. In another such embodiment, modulated dies in the entire swath are printed using the same value of the lithographic variable, which is different than the value of the lithographic variable at which reference dies are printed in the entire swath. In yet another such embodiment, modulated dies in the entire swath are printed using the different values of the lithographic variable. In this embodiment, reference dies in the entire swath are printed using an additional different value of the lithographic variable.

In some embodiments, acquiring the images includes acquiring images of the design pattern printed on a wafer using the reticle. In other embodiments, the images may include aerial images. Each of the embodiments of the method described above may include any other step(s) described herein.

Another embodiment relates to a different computer-implemented method for detecting and sorting defects in a design pattern of a reticle. This method includes acquiring images of the reticle for different values of a lithographic variable. The method also includes comparing at least two of the images. In addition, the method includes determining if individual pixels are different in the design pattern using results of the comparison. The method also includes determining if pixel differences in the at least two images follow a typical or atypical trend over the different values of the lithographic variable.

If pixel differences are determined to be present, the method may include assigning the location to a group based on comparison to a trend in a plot of one or more characteristics of the images of the defect as a function of the different values of the lithographic variable. For example, an atypical trend may be identified as a potentially relevant defect location. The images used in the method include, in some embodiments, images of modulated dies printed at the different values of the lithographic variable and images of reference dies printed using an additional different value of the lithographic variable.

An additional embodiment relates to another computer-implemented for detecting defects in a design pattern of a reticle. This method includes acquiring images of an entire swath of dies printed on a wafer using the reticle. At least two of the dies are printed at different values of a lithographic variable. The method also includes, subsequent to the acquisition of the images of the entire swath, comparing at least two of the images. In addition, the method includes determining if a defect is present in the design pattern using results of the comparison.

In one embodiment, the dies include modulated dies and at least one reference die. In another embodiment, the dies may include two or more reference dies as defined in the inspection recipe. In this embodiment, the method may also include generating a composite reference image from the images of the two or more reference dies. In such an embodiment, one of the at least two of the images used for the comparison includes the composite reference image. In an additional embodiment, the dies may include modulated dies and at least one reference die. Each of the embodiments of the method described above may include any other step(s) described herein.

Further embodiments relate to a carrier medium that includes program instructions executable on a computer system to perform any of the computer-implemented methods described herein. Additional embodiments relate to a system configured to perform any of the computer-implemented methods described herein. The system may include a processor configured to execute program instructions for performing one or more of the computer-implemented methods described herein. In one embodiment, the system may be a stand-alone system. In another embodiment, the system may be a part of or coupled to an inspection system such as a wafer imaging system or an aerial imaging measurement system. In a different embodiment, the system may be a part of or coupled to a defect review system. In yet another embodiment, the system may be coupled to a fab database. The system may be coupled to an inspection system, a review system, and/or a fab database by a transmission medium such as a wire, a cable, a wireless transmission path, and/or a network. The transmission medium may include "wired" and "wireless" portions.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
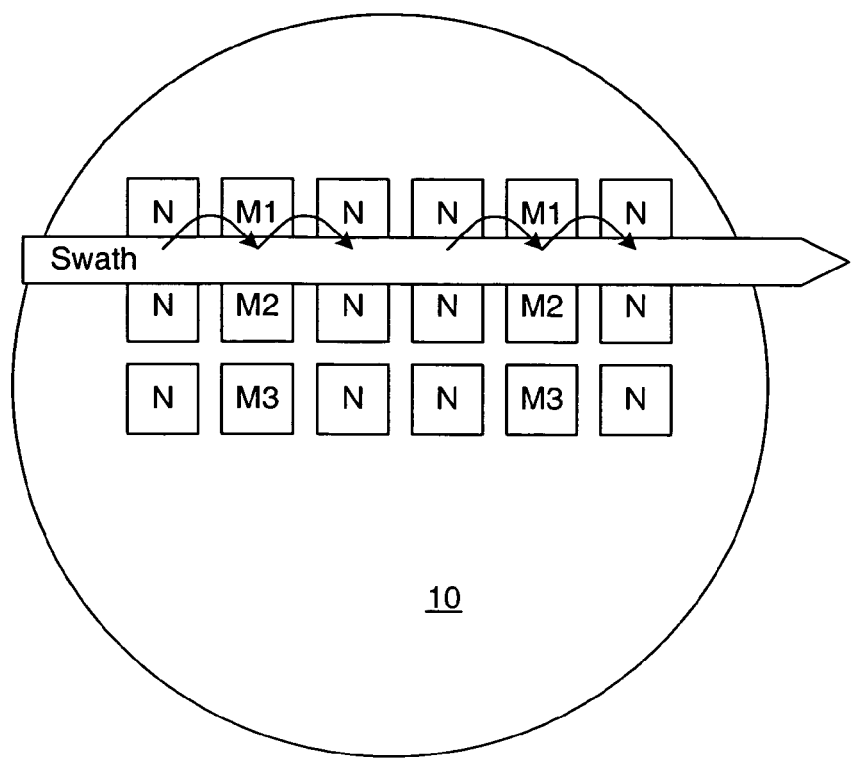
FIGS. 1-4a are schematic diagrams illustrating plan views of different configurations of dies printed on a wafer with a reticle for different values of a lithographic variable.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "defect" refers to a defect in a design pattern of a reticle that may cause a defect in a design pattern printed on a wafer using the reticle such as excessive corner rounding, unsatisfactory dimensions, missing features, bridging between features, etc. In particular, the methods described herein are particularly suitable for detecting defects in resolution enhancing technology (RET) features of the design pattern.

The terms "reticle" and "mask" are used interchangeably herein. A reticle generally includes a transparent substrate such as glass, borosilicate glass, and fused silica having a layer of opaque material formed thereon. The opaque regions may be replaced by regions etched into the transparent substrate.

Many different types of reticles are known in the art, and the term reticle as used herein is intended to encompass all types of reticles. For example, the term reticle refers to different types of reticles including, but not limited to, a clear-field reticle, a dark-field reticle, a binary reticle, a phase-shift mask (PSM), an alternating PSM, an attenuated or halftone PSM, and a ternary attenuated PSM. A clear-field reticle has field or background areas that are transparent, and a dark-field reticle has field or background areas that are opaque. A binary reticle is a reticle having patterned areas that are either transparent or opaque. Binary reticles are different from phase-shift masks (PSM), one type of which may include films that only partially transmit light, and these reticles may be commonly referred to as halftone or embedded phase-shift reticles. If a phase-shifting material is placed on alternating clear spaces of a reticle, the reticle is referred to as an alternating PSM, an ALT PSM, or a Levenson PSM. One type of phase-shifting material that is applied to arbitrary layout patterns is referred to as an attenuated or halftone PSM, which may be fabricated by replacing the opaque material with a partially transmissive or "halftone" film. A ternary attenuated PSM is an attenuated PSM that includes completely opaque features as well.

A reticle, as described herein, may or may not include a pellicle, which is an optically transparent membrane that seals off the reticle surface from airborne particulates and other forms of contamination. The term reticle may also be used to refer to a reticle that includes optical proximity correction (OPC) features. OPC features are designed to reduce distortions of an image printed using the reticle by reducing optical proximity effects. The term "optical proximity effects" generally refers to variations in lateral dimensions or shapes of printed features due to the proximity of other features on the reticle. Such effects may be reduced by determining the distortions due to the optical proximity effects and altering the features on the reticle to compensate for such distortions.

RET such as OPC are increasingly being applied to integrated circuit (IC) designs in order to print features on device wafers which are smaller than the wavelength of light used as the exposure source. These RETs often involve the addition of extra features to the design including sub-resolution assist features (SRAF) and serifs with the result that the layout of the design on the photomask or reticle becomes extremely complex. Verifying that the RET features will print correctly on the reticle and that the SRAFs will not print on the wafer but will cause the main features to print correctly on the wafer is becoming an increasingly difficult task. Furthermore, optical effects such as mask error enhancement factor (MEEF) may cause additional distortion of the final image at the wafer level. MEEF may be generally defined as the ratio of the critical dimension of a feature printed in a resist to the critical dimension of a structure formed on a reticle.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, and a conductive material. A "resist" may include any material that may be patterned by an optical lithography technique, an e-beam lithography technique, or an X-ray lithography technique. Examples of a dielectric material may include, but are not limited to, silicon dioxide, silicon nitride, silicon oxynitride, and titanium nitride. Additional examples of a dielectric material include "low-k" dielectric materials such as Black Diamond™ which is commercially available from Applied Materials, Inc., Santa Clara, Calif., and CORAL™ commercially available from Novellus Systems, Inc., San Jose, Calif., "ultra-low k" dielectric materials such as "xerogels," and "high-k" dielectric materials such as tantalum pentoxide. In addition, examples of a conductive material include, but are not limited to, aluminum, polysilicon, and copper.

One or more layers formed on a wafer may be patterned. For example, a wafer may include a plurality of dies, each having repeatable pattern features. Formation and processing of such layers of material may ultimately result in completed semiconductor devices. As such, a wafer may include a substrate on which not all layers of a complete semiconductor device have been formed or a substrate on which all layers of a complete semiconductor device have been formed. The term "semiconductor device" is used interchangeably herein with the term "IC." In addition, other devices such as microelectromechanical (MEMS) devices and the like may also be formed on a wafer.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

FIG. 1 illustrates one example of a configuration of dies printed on wafer 10 with a reticle for different values of a lithographic variable. In this example, reference or nominal dies N are printed on the wafer at a reference value for the lithographic variable that is being evaluated. The terms "reference die" and "nominal die" are used interchangeably herein. The reference value may be the best known value for the lithographic variable (e.g., best dose, best focus, etc.). Alternatively, the reference value may be any predetermined baseline value.

The lithographic variable that is being evaluated may include any lithographic parameter that may alter the design pattern that is printed on the wafer by the reticle. Examples of such lithographic variables include, but are not limited to, dose, focus, partial coherence, and numerical aperture. It may be particularly desirable to evaluate the effect that different values of focus will have on the design pattern since this is typically the lithographic parameter that will change most often over time for a lithography process.

As also shown in FIG. 1, modulated dies M1, M2, and M3 are printed on the wafer. The modulated dies are printed on the wafer at a value of the lithographic variable that is different than the reference value at which the nominal dies are printed. Although in the figure, the M1, M2 and M3 dies are in different rows, this is not a restriction of the invention. The different values at which the modulated dies are printed may vary depending upon, for example, the degree to which the lithographic variable may be varied (e.g., the smallest increment change in the lithographic variable that can be made on the lithography tool), the typical process window for the lithographic variable, and/or the number of modulated dies that can be printed on the wafer (e.g., in this example, the number of rows of dies that can be printed on the wafer). In one particular example, it may be desirable to evaluate how the design pattern will be printed across the typical process window of the lithographic variable for a lithography process. Therefore, the range of the values of the lithographic variable to be evaluated may be divided by the number of modulated dies that can be printed on the wafer to determine appropriate increments in the different values of the lithographic variable. However, appropriate values for the lithographic variable may be determined in any other manner.

Although three rows of dies are shown printed on the wafer in FIG. 1, it is to be understood that the number of rows of dies that are printed on the wafer will vary depending on, for example, the dimensions of the dies and the dimensions of the wafer. In addition, although two sets of dies (each set including an N-M-N sequence of dies) are shown in FIG. 1 to make up each row of dies, it is to be understood that the number of sets of dies in each row may also vary depending upon the dimensions of the dies and the dimensions of the wafer.

To inspect the design pattern, the dies in a row are imaged in a swath. The dies may be imaged using, for example, the wafer inspection system described herein or any other appropriate tool in the art such as wafer inspection systems that are commercially available from KLA-Tencor, San Jose, Calif. The dies in a row may be imaged in the swath direction shown in FIG. 1 or in the opposite direction.

After imaging two adjacent dies printed on the wafer, the images of the two dies will be compared as shown by the arrows in FIG. 1. In particular, the first nominal die in the swath is imaged and saved. After imaging the adjacent M1 die, the images of the nominal die N and the adjacent modulated die M1 are compared, and any differences between the two dies are saved or otherwise noted, recorded, stored, etc. The presence of defects in the dies may then be determined using the results of the comparison. For example, to determine if the differences between the two dies are defects, a threshold-type defect detection algorithm may be applied to the difference data to determine if the differences are indicative of defects.

The image of the M1 die may also be saved for comparison with the other adjacent nominal die N after imaging of this nominal die in the swath. Images of these two dies may then be compared as described above, and defects may be detected based on the results of the comparison as described above.

Since the modulated M1 die is compared with two reference dies, the configuration shown in FIG. 1 allows double detection of defects in the M1 die. In other words, if a randomly caused defect appears in the first reference die, then the differences between the images of the first reference die and the M1 die may indicate the presence of a defect in the M1 die even though the defect is actually present in the first reference die. However, the probability that the randomly caused defect will appear in the same position in the second reference die is substantially low. Therefore, when the image of the M1 die is compared to the second reference die, the defect that was found in the first comparison will most likely not be found in the second comparison. As such, defects that are found in only one of the two comparisons may be labeled as false defects and may be eliminated from any further evaluation.

Although the "double detection" of defects that is provided by comparing each modulated die with two different nominal dies effectively reduces the number of false defects that are detected, there are some disadvantages to such methods. For example, a substantial amount of space on the wafer is used for printing nominal dies thereby reducing the number of modulated dies that can be printed on the wafer, which in turn reduces the number of different values of the lithographic variable that can be evaluated. Therefore, it would be advantageous to reduce the number of reference dies that are printed on the wafer without reducing the accuracy of the defect detection method.

Several improvements to the above-described defect detection method are described below. It is important to note that each improvement may be used alone or in combination with one or more of the other improvements.

One improvement can be realized by increasing the number of dies that can be imaged and processed simultaneously. For example, as described above, two dies are imaged (a nominal die and a modulated die), the images of the two dies are compared to detect differences between the images, and the differences are examined to identify those differences that indicate defects. Therefore, only two dies are processed at one time. In an alternative, three dies may be imaged (two nominal dies and one modulated die), and these images may be processed simultaneously or in "real time" to detect defects in the modulated die.

It would be advantageous, however, if more image data could be processed simultaneously. For example, according to one embodiment, the images that are acquired may include images of an entire swath of dies printed on a wafer using the reticle. The images of the entire swath of dies can then be examined by the inspection algorithm before flagging defects. In other words, any useful or meaningful comparisons between any of the dies in the entire swath may be made prior to analyzing the differences between the images for defect detection. In addition, the die layout in the swath will be known a priori. In this manner, the computer-implemented method may select the appropriate die images for comparison based on the position of the die images within the swath. In another embodiment, a user with knowledge of a layout of dies printed on a wafer can select which of the images are used for the comparison.

Although imaging an entire swath of dies at one time generates a substantial amount of data that must then be handled as described herein for defect detection, image computers such as those described in U.S. patent application Ser. Nos. 10/967,388 to Bhaskar et al. filed Oct. 18, 2004, 10/967,397 to Bhaskar et al. filed Oct. 18, 2004, 10/967,542 to Bhaskar et al. filed Oct. 18, 2004, 10/967,419 to Bhaskar et al. filed Oct. 18, 2004, 10/967,375 to Blecher et al. filed Oct. 18, 2004, 10/967,838 to Bhaskar et al. filed Oct. 18, 2004, 10/967,500 to Bhaskar et al. filed Oct. 18, 2004, 10/967,376 to Dubiner et al. filed Oct. 18, 2004, 10/967,420 Miller et al. filed Oct. 18, 2004, 10/967,832 to Miller et al. filed Oct. 18, 2004, and 10/967,418 to Bhaskar et al. filed Oct. 18, 2004, which are incorporated by reference as if fully set forth herein, may be used to handle such a substantial amount of data.

Figure 2:
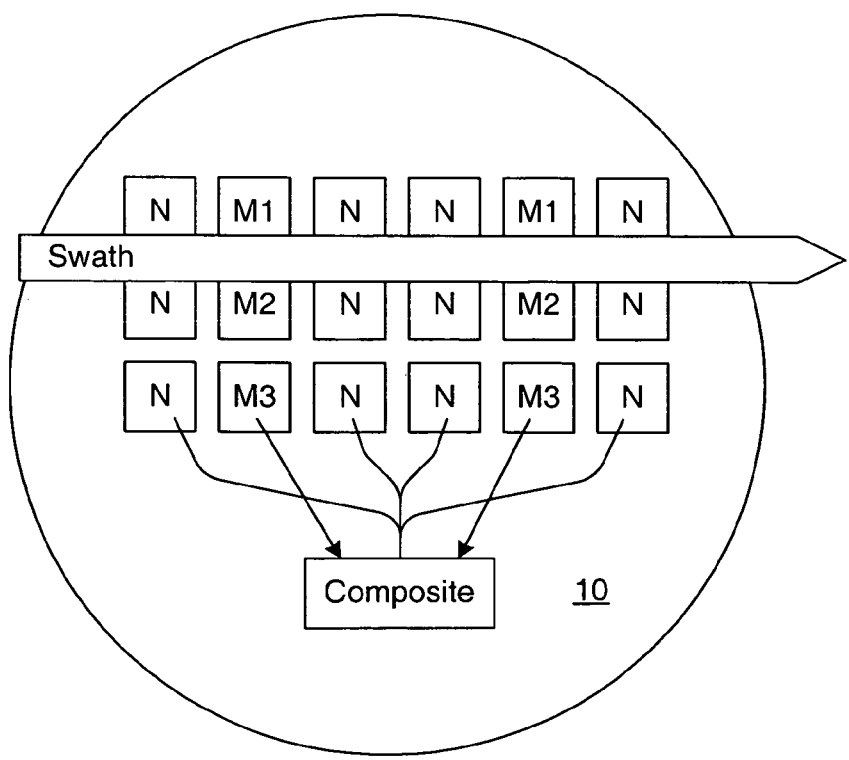

Being able to simultaneously process image data from an entire swath of dies on a wafer provides several advantages. For example, image data may be acquired for the entire swath including two or more reference dies obtained at nominal values and one or more modulated dies. If two or more reference dies are included in the swath, the methods described herein may include generating a composite reference image from the two or more reference images. For example, as shown in FIG. 2, a composite reference image may be generated from all four of the reference dies included in a swath. However, the composite reference image may be generated from fewer than all of the reference dies in the swath. In addition, as shown in FIG. 2, a composite reference image may be generated from the reference dies in one swath on the wafer, and other composite reference images may be generated for other swaths on the wafer. In this manner, a composite reference image may be generated in real time after each swath is imaged. However, a composite reference image may alternatively be generated from two or more reference dies, and the same composite reference image may be used for defect detection in modulated dies in the same or different swaths on the wafer.

The composite reference image may be generated in any manner known in the art (e.g., averaging the image data of the two or more reference dies). In addition, it may be desirable to align the individual reference die images prior to generating the composite reference image. In one example, the reference die image frames in a swath may be aligned to a common coordinate reference, and any misalignment in the frames may be corrected by sub-pixel interpolation of pixel values. The modulated dies may be aligned in a similar manner.

In any case, the composite reference image may be used for comparison with the modulated dies in the swath as shown by the arrows in FIG. 2. In other words, one of the at least two images used for comparison may include the composite reference image. Using a composite reference image for defect detection exploits the presence of multiple nominal dies in a swath to improve the stability of the reference image against which each of the modulated dies is compared. The use of a composite reference image may also improve the sensitivity of the detection by reducing the effects of random noise that may be present in the individual reference die images. In other words, the methods described herein are advantageous in that the signal-to-noise ratio of the data used for defect detection may be increased, which may in turn lead to the ability to isolate the most likely relevant defects.

Using the composite reference image for comparison with the modulated die images may also advantageously allow the number of reference dies included in the swath to be reduced. For example, as described above, double defect detection is advantageous in that it allows false defects caused by defects in the reference die instead of the modulated die to be eliminated from the detection results thereby increasing the accuracy of the defect detection methods. However, when the composite reference image is generated from two or more reference images, any differences between the reference images may be detected, and these differences may be analyzed to determine if defects are present in the reference images. Any defects that are determined to be present in one or more of the reference images may then be removed from the image data of the individual reference dies. The "scrubbed" image data may then be used to generate the composite reference image.

It is important to note that in the methods described herein, if an entire swath of die images can be generated and processed simultaneously, the reference image that is used for comparison may be the composite reference image as described herein or an individual reference image. Even if two or more non-composite reference images are used for comparison to modulated dies, the number of reference dies in the swath can be reduced from the number currently being used in the N-M-N configuration since the individual reference die images can be used and reused for comparison to modulated die images regardless of the position of the reference and modulated die images in the swath.

Using fewer nominal dies on a wafer advantageously allows more space on the wafer to be used for modulated dies. Therefore, by using data more efficiently and thoroughly, the methods described herein are able to inspect more examples of dies that are modulated and fewer examples of reference dies. One other inspection technique that can be used to reduce the number of reference dies that are printed on a wafer is to compare the modulated dies to a golden die image that is constructed from design information or prior scanning and then stored on some medium such as a database. Efficient data use as described herein, however, is potentially a more cost effective, accurate, and faster method than using golden die images from a database.

Figure 3:
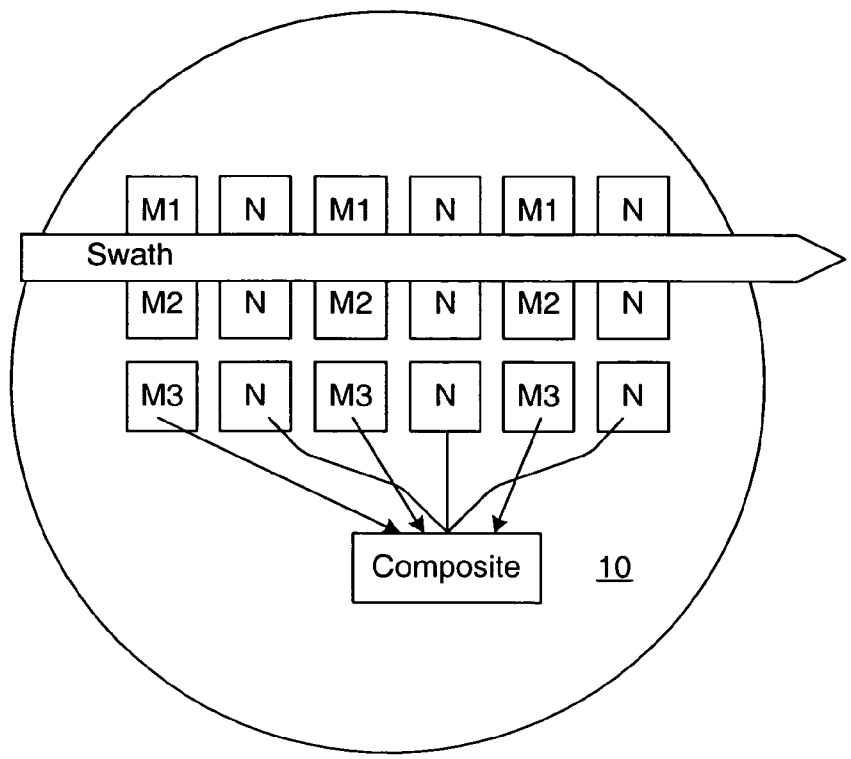

Unlike the configurations of the dies shown in FIGS. 1 and 2, when fewer nominal dies can be used without reducing the accuracy of the detection method, the number of modulated dies may be increased. One such configuration is illustrated in FIG. 3. In this configuration, the number of modulated dies in a swath is equal to the number of reference dies in the swath. In addition, every other die position includes a different type of die in an N-M-N-M configuration. However, the modulated and nominal dies may be arranged in any other manner in the swath. For example, the first two dies in the swath may be reference dies, and all other dies in the swath may be modulated dies. In any case, reducing the number of reference dies used by the method allows more modulated dies to be printed on a wafer thereby allowing the design pattern of the reticle to be examined for defects at more values of the lithographic variable being altered.

As shown in FIG. 3, the reference die images in a swath may be used to generate a composite reference image. The composite reference image may be generated as described above. In addition, the composite reference image may be used for comparison with the acquired images of the modulated dies as described above. In addition, as shown in FIG. 3, images of each of the reference dies in an entire swath may be used to generate the composite reference image. Alternatively, images of fewer than all of the reference dies in an entire swath may be used to generate the composite reference image. Furthermore, as described above, a composite reference image may be generated for each swath on the wafer that is imaged. Alternatively, one composite reference image may be generated and used for comparison to images of modulated dies in more than one swath on the wafer.

As further shown in the configuration of FIG. 3, modulated dies in the entire swath may be printed using the same value of the lithographic variable. In particular, each of the modulated dies in one swath are M1 modulated, each of the modulated dies in another swath are M2 modulated, etc. In other words, if the lithographic variable that is being evaluated is focus, each of the M1 modulated dies may be printed at the same focus value, each of the M2 modulated dies may be printed at a different focus value that is the same for each M2 die, and so on. The value of the lithographic variable used to print the dies in each swath is also preferably different than the value of the lithographic variable used to print the reference dies such that meaningful comparisons may be made between the modulated dies and the reference dies.

Imaging an entire swath having the configuration shown in FIG. 3 and performing defect detection as described above allows multiple similarly modulated dies to be inspected at the same time. Performing defect detection for more than one die modulated in a similar manner provides more information about the design pattern and the defects detected in the design pattern. For example, defects may be identified as randomly occurring defects if the defect shows up in fewer than all of the similarly modulated dies. Using the configuration shown in FIG. 3, therefore, an entire swath may be imaged, and these images may be used to detect defects in dies having the same value of the modulated lithographic variable.

Figure 4:
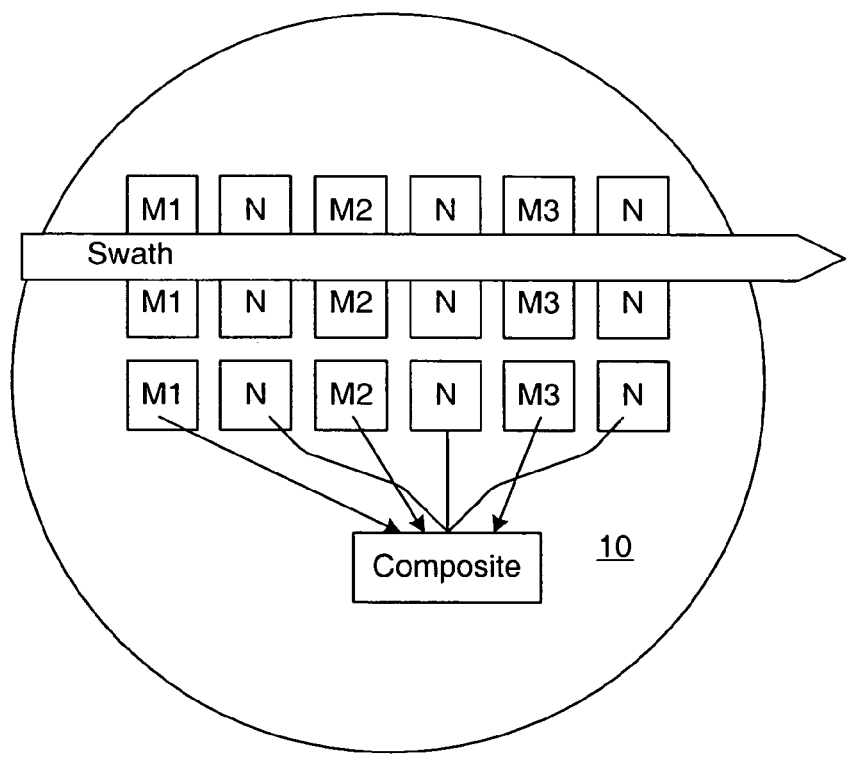

A different configuration is illustrated in FIG. 4 in which the modulated dies in one swath have different values of the modulated lithographic variable. In other words, the dies are laid out such that the modulation varies along a row rather than in a column as shown in FIGS. 1-3. In particular, the modulated dies in one swath may be M1 modulated, M2 modulated, M3 modulated, and so on. In this manner, if the lithographic variable that is being evaluated is focus, the focus at which the M1 die is printed may be 0.1 µm, the focus at which the M2 die is printed may be 0.2 µm, the focus at which the M3 die is printed may be 0.3 µm, and so on. It is to be understood that these focus values are merely intended to be examples of modulated focus values for illustrative purposes and are not to be interpreted as limiting or otherwise exemplary examples. The value of the lithographic variable used to print the modulated dies in each swath is also preferably different than the value of the lithographic variable that is used to print the reference dies such that meaningful comparisons may be made between the modulated dies and the reference dies.

Imaging an entire swath having the configuration shown in FIG. 4 and performing defect detection as described above allows differently modulated dies to be inspected at the same time. Therefore, this configuration may be advantageously used to examine defects in the design pattern across an entire range of values of the lithographic variable in one swath. As such, one swath may be imaged and a substantial amount of defect data may be generated from the imaged swath in a relatively short amount of time. In addition, since the swath may include substantially more modulated dies than was previously available, the modulated dies in one swath may be printed at values of the lithographic variable spanning an entire typical process window for the reticle. In this manner, one swath may be imaged, and the swath image may be used to examine the process window of the reticle in a substantially short amount of time, particularly when compared to previously used process window qualification methods.

Figure 5:
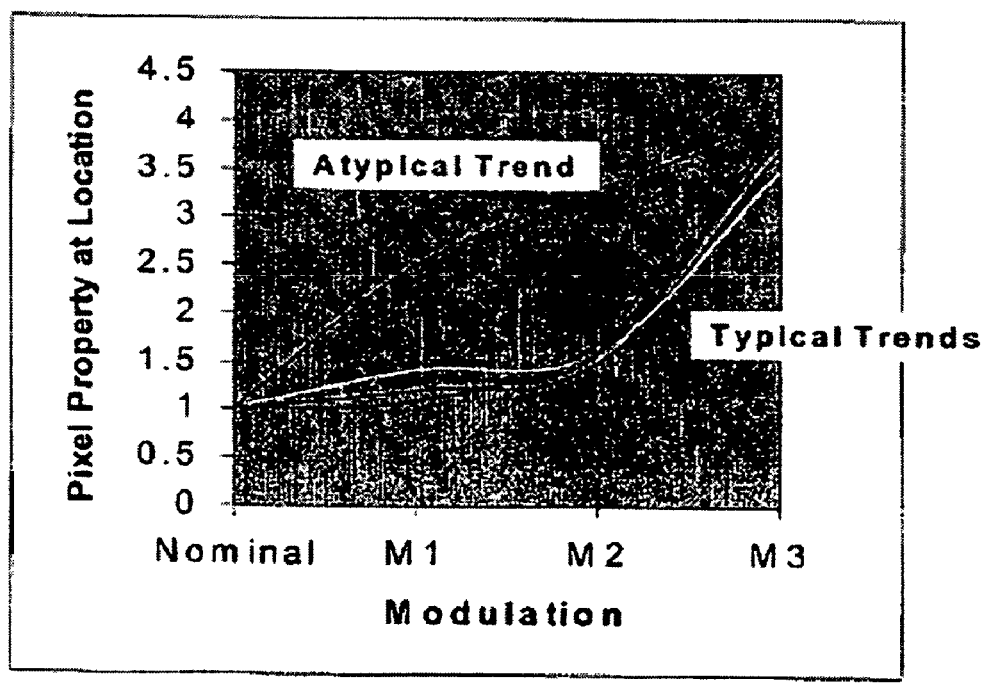
FIG. 5 is a graph illustrating examples of different trends in plots of a characteristic of images of defects as a function of different values of a lithographic variable.

The configuration shown in FIG. 4 may also be used to examine the entire trend of any pixel property as a function of modulation at each pixel location (x, y). A "trend" may be generally defined as how a characteristic of images at a particular pixel location such as pixel intensity varies as a function of different values of a lithographic value. As such, trends at particular pixel locations may be expressed by a plot such as those shown in FIG. 5. As shown in FIG. 5, a number of trends that are relatively similar for a particular property at a pixel location as a function of modulation may be defined as "typical trends." Whether or not these "typical trends" are indicative of non-defective pixel properties may be established in advance by another method (e.g., defect review). The "typical trends" may be established experimentally through wafer or aerial image experiments or empirically through simulations (e.g., aerial image simulation).

Trends that appear to be atypical may be flagged as potential defects of interest or a potentially relevant defect location. In another embodiment, defects may be detected by comparing at least two images printed or acquired at different values of a lithographic variable. The images may include images of modulated dies printed at different values of a lithographic variable and images of reference dies printed using an additional different value of the lithographic variable as described herein. In some embodiments, if a defect is determined to be present, the method may include assigning the defect to a group based on a trend in a plot of one or more characteristics of the images of the defect as a function of the different values of the lithographic variable.

The trend-based defect detection method described above is based on the assumption that line width variations and line-end pull backs that occur as a function of modulation will affect a larger number of pixels and follow certain trends while the occasional "short" or other anomalous events will occur in smaller numbers and follow a different trend. Therefore, it is clear that different defect detection methods may be used in the methods described herein to exploit information from multiple modulated dies in a single swath. In addition, the trend-based defect detection method described above may be performed for differently modulated dies in a single swath or differently modulated dies in different swaths. In other words, the trend-based defect detection method may be used regardless of the die configuration on the wafer. Furthermore, the trend-based defect detection method may advantageously detect defects of interest (DOIs) while ignoring the large number of unimportant image differences (such as line width variations, line-end pull-backs, etc.) that will also occur as the lithographic variable is modulated.

In another example of a trend-based defect detection method, a point-to-point inspection on a relatively high resolution tool such as a critical dimension scanning electron microscope (CD SEM) or a Review SEM could be used to perform measurements and/or defect detection from the nominal die outward in the modulated dies. In other words, a point-to-point inspection based on the PWQ-type defect detection results may be performed. This inspection of the PWQ-type defects may be performed for the nominal dies and the modulated dies up to the point of failure in the design pattern. The corresponding points in the nominal and modulated dies that exhibit normal or expected variation or degradation may be filtered out as non-defective or irrelevant. Any remaining defects at these points may be classified (e.g., using automatic defect classification (ADC)) to look for bridging or other defect types that are relevant to process window errors. For example, for measurements such as CD measurements, the method may include determining if a "normal" variation in the CD measurements is present. This determination may be made using a recipe based on the predominant feature direction (the predominant trend in the feature characteristic being measured). As such, relevant variations in the feature could be distinguished from irrelevant variations in the feature. In a further example, for defect detection, an ADC type inspection could be used to search for classic kinds of failure in the design pattern such as bridging features.

Figure 4A:
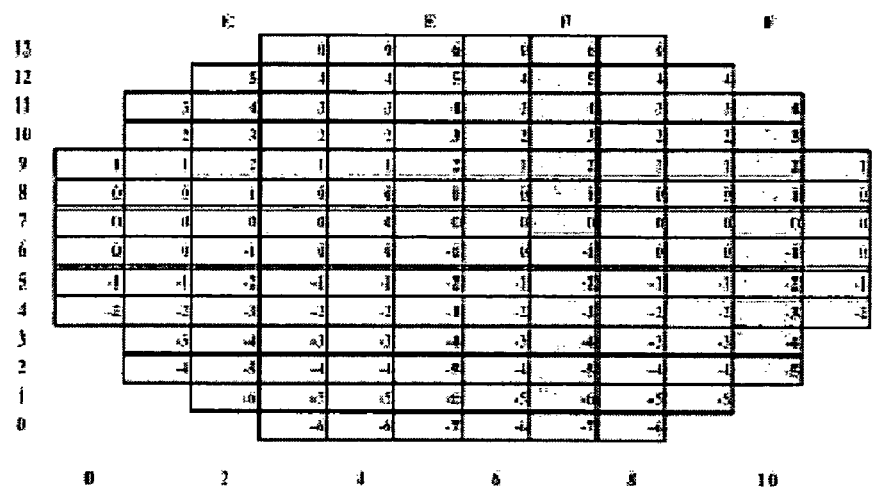

FIG. 4a illustrates another die configuration that can be used as described herein. In this configuration, exposure dose, E, can be modulated in column 2. PWQ type defects can be detected by comparison of the dies in column 2 with a corresponding die in columns 0, 1, and/or 3. The exposure dose can also be modulated in column 5. Defects can be detected by comparing the dies in column 5 with the corresponding reference dies in columns 3 and/or 4. In addition, exposure and dose modulation may be examined on one wafer. For example, as shown in FIG. 4a, focus, F, may also be modulated in columns 7 and 10 on the wafer. Defects may be detected in these modulated dies by comparison of the dies with reference dies in the corresponding rows of columns 8, 9, and/or 11. In this manner, modulation of exposure dose and focus may be examined separately on one wafer. The die configuration shown in FIG. 4a may be further configured as described herein.

Each of the die configurations described herein may be used by a computer-implemented method to detect and/or sort defects in a design pattern of a reticle. In particular, the die configurations described herein may be used in PWQ-type defect detection methods. For example, as described above, images of the reticle for different values of a lithographic variable may be acquired. In particular, acquiring the images may include acquiring images of the design pattern printed on a wafer using the reticle. These images may be acquired using, for example, the system described herein. In addition, at least two of the images may be compared. The method also includes determining if a defect is present in the design pattern of the reticle using results of the comparison.

As noted above, however, a relatively large number of unimportant or irrelevant image differences may be detected due to the very nature of the methods described herein. The large number of unimportant differences can result in the detection of a relatively large number of irrelevant defects and false defects. The detection of irrelevant and/or false defects in such large numbers may have several disadvantages. For example, in order to identify the defects of interest, a user or a software program would have to sort through all of the irrelevant and/or false defects. Obviously, such sorting of the detected defects would reduce the throughput of the process of finding defects of interest.

As further noted above, the trend-based defect detection method may be used to differentiate between meaningful defects (or defects of interest) and irrelevant defects. It may also be advantageous to quickly and accurately differentiate between defects of interest and irrelevant defects after the defect detection has been performed. In other words, it may be desirable to perform defect classification to distinguish between defects of interest and irrelevant defects. One problem with currently used defect classification methods for use with the type of defect data that is generated as described herein is that the defect classification methods tend to focus on characteristics of the defects themselves to identify the classification to which the defect belongs. In particular, due to the modulation of the lithographic variable, the same defect may appear differently in differently modulated dies. Therefore, one defect may be assigned different classifications depending on the die in which it is detected.

According to one embodiment, a more accurate and useful defect classification method for the PWQ based defect detection methods described herein may use one or more characteristics of a region proximate the defect (i.e., the "background" information) to classify defects. For example, the method may include isolating the immediate neighborhood of the background (which could be called a "micro-region") and comparing the immediate neighborhood to others using standard correlation and template matching algorithms, which may be any suitable algorithms known in the art of image processing. The micro-region may be defined by a 16×16 pixel image centered on the defect or containing the defect. Alternatively, the micro-region may be defined by a 32×32 pixel image centered on the defect or containing the defect. In some embodiments, the region proximate the defect may be a "greater neighborhood" region of about 64 pixels×64 pixels.

In another example, instead of using acquired image data to define the background proximate the defect, the defect location may be determined in the GDS file of the design pattern (decorated or un-decorated with RET features). A portion of the design pattern data in the GDS file proximate the defect may be selected. The background in the GDS file may be compared to other defective locations as is done with the reference die images. The additional locations can then be correlated to the defect location from the original inspection. The additional locations may also be designated for review (e.g., by SEM).

In yet another example, the region proximate the defect may be generated through aerial projection. In one such example, the aerial image data may be taken from an aerial sensor such as that described in co-owned, co-pending U.S. patent application Ser. No. 10/679,857 filed Oct. 6, 2003 by Stokowski et al., which is incorporated by reference as if fully set forth herein. Alternatively, the aerial image data could be generated by an aerial image sensor of the type described in U.S. Pat. No. 6,803,554 to Ye et al. and U.S. Pat. No. 6,807,503 to Ye et al. and U.S. Patent Application Publication No. US 2003/0226951 by Ye et al., which is incorporated by reference as if fully set forth herein, which are incorporated by reference as if fully set forth herein.

By using the background features around and "behind" the defects, the methods described herein are able to find the relevant changes in the lithographic feature that can be lost in irrelevant defects using other methods. As used herein, the term "background" refers to features of the reference image that are immediately "behind" the defect image (i.e., the features of the reference image or the design pattern data that are located at the same pixel locations as the defect in the image of the modulated die) and the region around the defect image (i.e., the features of the image of the modulated die proximate the defect). In this manner, by combining the results of "background binning" (e.g., grouping defects on the basis of one or more characteristics of a region proximate the defect) with PWQ type defect detection methods for ordering the results of the repeating defect detection algorithm and prioritized die information, the methods described herein are able to present the user with information that can be used to find critical or relevant defects faster than existing defect detection methods.

According to one embodiment, therefore, a computer-implemented method for sorting defects in a design pattern of a reticle includes searching for defects of interest in inspection data using priority information associated with individual defects in combination with one or more characteristics of a region proximate the individual defects. The one or more characteristics of the region (i.e., the background information) may be selected by a user. The inspection data is generated by comparing images of the reticle generated for different values of a lithographic variable. The images include at least one reference image and at least one modulated image. In this manner, the method involves searching a relatively large amount of defect information for defects of interest using the priority information generated by PWQ type inspection in combination with the background information. The priority information corresponds to a modulation level associated with the individual defects.

The method also includes assigning one or more identifiers to the defects of interest. In one embodiment, the one or more identifiers may include an indicator identifying if the defects of interest are to be sampled. In one such embodiment, assigning the identifier(s) may be performed automatically based on the priority information and the one or more characteristics of the region proximate the individual defects. In another embodiment, the identifiers may include one or more defect classifications. The classifications may distinguish defect types using user defined names in some embodiments. Assigning identifier(s) to the defects may be performed as further described herein.

In some embodiments, the method may include grouping the defects of interest based on the priority information, the one or more characteristics of the region proximate the individual defects, or a combination thereof. In another embodiment, the method may include grouping the defects of interest based on the one or more characteristics of the region proximate the individual defects in combination with one or more characteristics of the defects of interest. Grouping the defects in these embodiments may be performed as further described herein.

In this manner, the methods described herein may be used to find a relatively small number of defects of interest from a large amount of candidate defects. The inputs to the method may include defect priorities, defect attributes, correlation to critical points from DRC, and defective and reference images. The candidate defects may be filtered based on the defect priorities and/or attributes to reduce the number of candidate defects that are searched. In some embodiments, the features of the defects and the background may be obtained and compressed for search. The outputs of the method may include defects of interest with class codes and review sample flags or any other identifiers known in the art. The defects that are not of interest may be excluded from the inspection data such that the number of defect candidates that are searched is reduced.

The embodiments of the method described above may include any other steps described herein. For example, the method may include retrieving or finding similar defects based on search criteria and given defect examples. In addition, the method may include performing a number of functions to prepare for defect review such as providing status and feedback to a user, generating charts for defect population in terms of groups, classes, and/or priorities, generating tags for defect priorities and review samples, generating a defect list with defect information, and generating folders for classified or excluded defects. In addition, the method may include sampling defects for later processing, which may be performed as described herein, and which may reduce the number of defect samples that are reviewed or processed. Furthermore, as described further herein, the methods may be customized by the user depending on, for example, the defects of interest by changing criteria for filtering, grouping, retrieving, classifying, sampling, manually overriding the results of automated operations, and repeating any step(s) at any time.

For example, in one embodiment, if a defect is determined to be present in the design pattern of a reticle, the computer-implemented methods described herein may include assigning the defect to a group based on one or more characteristics of a region proximate the defect. Grouping can be performed by either supervised or unsupervised classification techniques, which are known in the art of pattern recognition. The one or more characteristics of the region that are used for assigning the defect to a group may include one or more characteristics of the design pattern in the region. In addition, the one or more characteristics of the region that are used for assigning the defect to a group may include one or more characteristics of the region in one or more images used for the comparison. In other words, the characteristic(s) of the region may include the characteristic(s) of the region in the modulated die in which the defect was detected in addition to the characteristic(s) of the corresponding region in the one or more reference dies that were compared with the modulated die. The characteristic(s) of the region that are used for sorting the defects into groups may also be selected by a user. The user may select the characteristic(s) prior to grouping the defects as described further herein.

In one embodiment, assigning the defects to a group may include comparing an image of the region proximate the defect to images of the regions that are proximate to other defects detected in the design pattern. In another embodiment, a portion of a modulated die image proximate the defect may be located in a GDS file image of the design pattern. The portion of the GDS file image corresponding to the portion of the modulated die image proximate the defect may be compared to other similar locations in the modulated die image.

In addition, the portion of the GDS file image or other design layout mapped to the defect may be used to determine one or more characteristics of the region proximate the defect. These characteristics may be determined using any other images or data such as a high resolution image of the design pattern of the reticle. A high resolution image of the design pattern may be obtained using any high resolution reticle imaging system known in the art. In another embodiment, a simulated aerial image of the design pattern of the reticle may be used to determine one or more characteristics of the region proximate the defect. The simulated aerial image may be generated using any suitable simulation program known in the art. In a different embodiment, the one or more characteristics of the region proximate the defect may be determined from an aerial image of the reticle obtained using an aerial imaging and measurement system (AIMS) as described further herein.

Examples of methods that may be used for classification of the defects are illustrated in U.S. patent application Ser. No. 10/954,968 to Huet et al. filed on Sep. 30, 2004, which is incorporated by reference as if fully set forth herein. Examples of additional methods that may be used for sorting and classifying defects are illustrated in U.S. Patent Application Ser. No. 60/618,475 to Teh et al. filed on Oct. 12, 2004, which is incorporated by reference as if fully set forth herein.

After sorting the defects into groups, the method may include assigning a defect classification to one or more defects or the entire group. The same classification can be assigned to defects in different groups. Classification of the different groups of defects may include analyzing one or more characteristics of one or more defects in the group. For example, the method may include analyzing one or more characteristics of one or more defects in the group to determine if the group of defects is an irrelevant defect group. The method may also include analyzing one or more characteristics of one or more defects in the group to determine if the group indicates a failure in the design pattern. Classifying the different groups of defects may also or alternatively include analyzing one or more characteristics of the background features around and behind the defects.

The methods described herein may also include a number of other filtering and/or sorting functions. For example, the method may include comparing the defects of interest to inspection data generated by design rule checking (DRC) performed on design pattern data of the reticle to determine if the defects of interest correlate to DRC defects. In one such embodiment, the method may include removing from the inspection data the DRC defects that do not correlate with the defects of interest.

In such embodiments, the locations of the defect are correlated to known vulnerable points based on the results of DRC. DRC can produce a list of critical points (sometimes referred to as "hot spots"). These points can be used alone, directly as a guide for inspection and/or measurements of reticle design pattern. However, the DRC often produces too many points for inspection and/or measurement. Therefore, the critical points identified by the DRC can be filtered as described herein using one or more characteristics of a region proximate the critical points alone to reduce the population of the critical points. In addition, or alternatively, the critical points may be filtered using the "Defects Like Me" function described herein to reduce the population. In this manner, inspecting, measuring, and/or reviewing critical points that are similar may be reduced, and even eliminated.

In addition, the critical points identified by the DRC may be overlaid with the inspection data generated as described herein. The inspection data may be data generated by imaging a wafer on which one or more modulated dies and one or more reference dies are printed. Alternatively, the inspection data may include aerial images of the reticle design pattern generated by simulation or experimentation. In this manner, the defects of interest found as described herein may be compared to inspection data generated by design rule checking to determine if the defects of interest correlate to design rule checking defects. The inspected defects that do not correlate with the DRC results may then be removed from the inspection data. In each of the examples provided above, ORC results may be used instead of DRC results.

The background binning methods described above have been shown to group the defects effectively such that the relevant defects can be found faster. In the case of PWQ methods, the background is sometimes the only relevant feature group, and so during a PWQ experiment, the system can use this feature set to group defects with similar backgrounds into the same bins. These background features may be divided into a number of different subgroups (e.g., three subgroups), which may be presented to users on a graphical user interface (GUI) such as those described herein. The different subgroups may include, for example, statistic measures of image intensity, statistic measures of image intensity variation, and measures of elementary image structures. Users can choose a combination of background subgroups to use in the PWQ binning.

Figure 6:
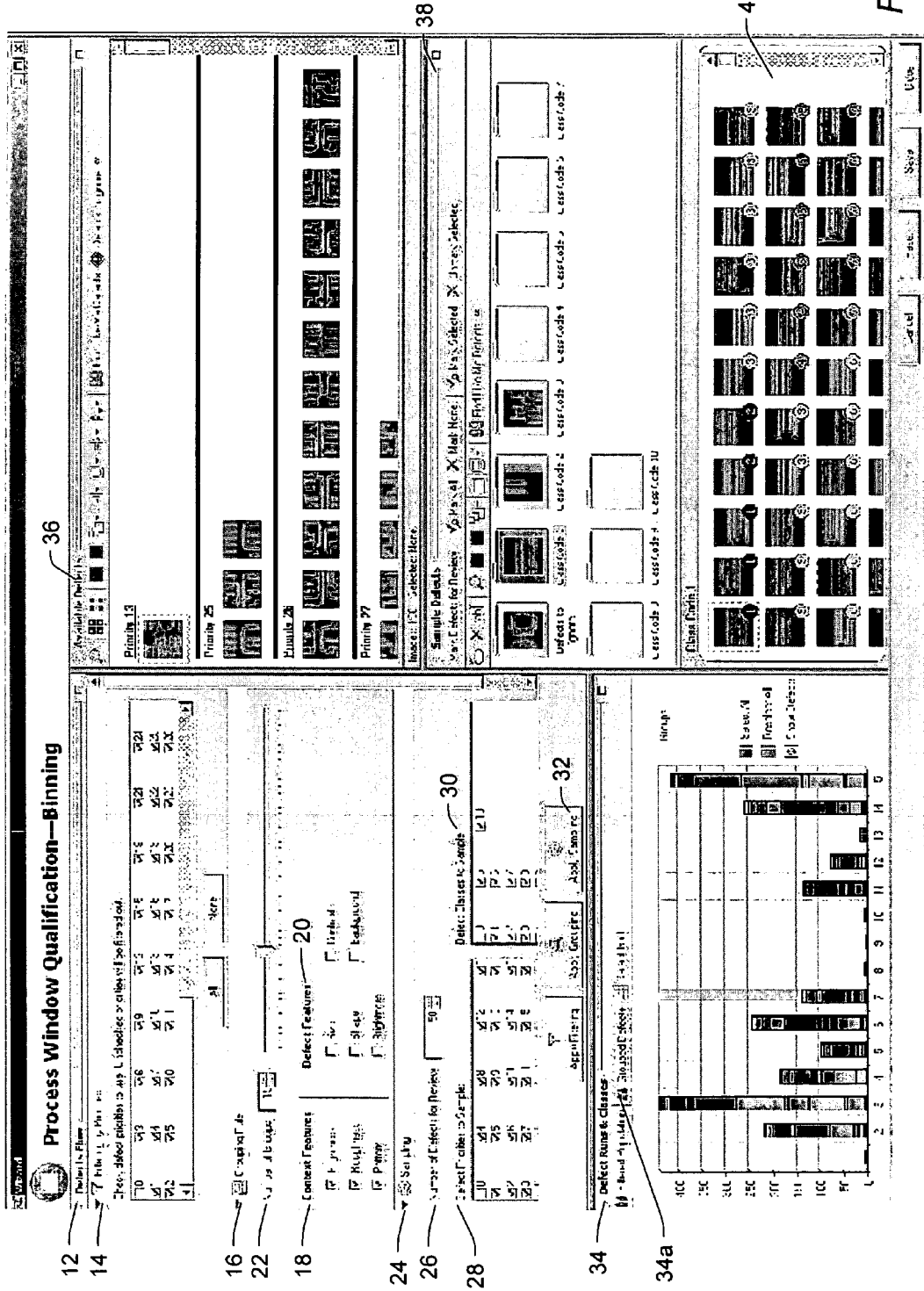
FIGS. 6-7 are screenshots illustrating examples of different user interfaces that can be used to sort defects detected by the methods described herein.

FIG. 6 is a screenshot illustrating one example of a user interface that can be used to sort defects detected by the methods described herein. In particular, a user will be able to choose which subgroups of background to use for binning of the defects, and FIG. 6 illustrates one possible user interface for selecting the subgroups. As shown in FIG. 6, the user interface includes Defects Flow box 12, which includes a number of options for the user. For example, Defects Flow box 12 includes Filtering by Priorities section 14. In this section, the user may select the defect priorities to use for filtering. The priorities may be selected individually by clicking on the boxes next to the priority numbers. Alternatively, the user may select all priorities or none of the priorities by clicking one of the buttons below the listing of the individual priorities.

The PWQ defects are prioritized by the modulation level (e.g., M1, M2, M3, etc.) where they were first detected (as determined in the setup of the experiment) and within modulation by the number of occurrences of the defect found in all modulated dies through the repeater stacking of all of the defects in the same modulation direction, positive or negative from nominal. Such prioritization of the defects is further described in U.S. Patent Application Publication No. US2004/0091142 to Peterson et al., which is incorporated by reference as if fully set forth herein. In the user interface, the user is able to filter by this priority or select defects with certain priorities to work with in Filtering by Priorities section 14. Defects that do not fall within the selected priorities may be eliminated from the defect data.

Figure 6A:
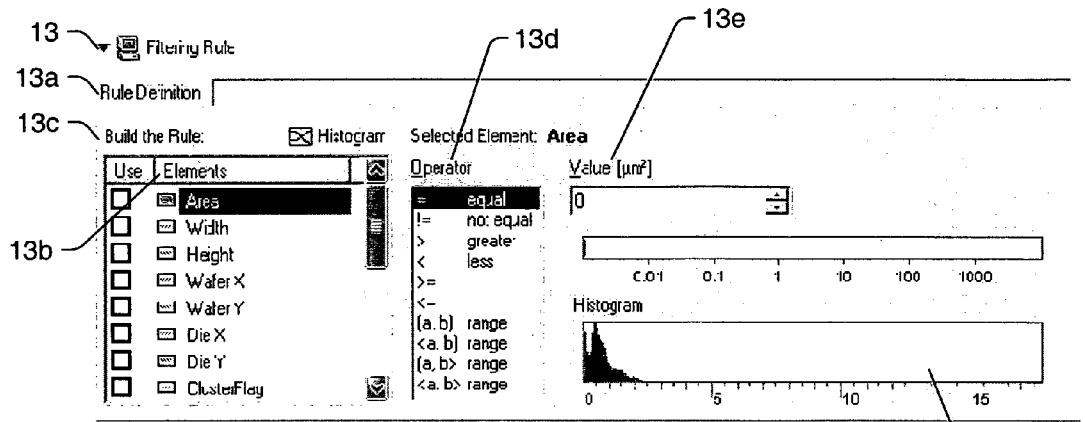

In another embodiment, the defects may be filtered using one or more rules. The one or more rules may be based on, for example, one or more characteristics of the defects. In one embodiment, the user may create the rules that are used to filter the defects. For example, as shown in FIG. 6a, the user interface may include Filtering Rule box 13. The Filtering Rule box allows the user to create a filtering rule in a number of different ways. For example, the user may enter a rule definition in Rule Definition 13a section of the Filtering Rule box. In addition, the user may select one or more elements 13b in Build the Rule section 13c by checking the box beside those elements that are to be used to filter defects. Although a number of different elements are illustrated in FIG. 6a, it is to be understood that the elements that are displayed in the Build the Rule section may vary depending on, for example, the defect characteristics that are of interest.

Depending on the element that is selected, a number of different operators may be displayed in Operator section 13d. The user may select an operator to be used with the selected element. The user may select the operator by clicking on an operator or in any other manner known in the art. In addition, the user may enter a value in Value section 13e that is to be used with the selected element and operator. The values that are available for selection may vary depending on the element and the operator that were previously selected. Once the user has selected an element and operator, Histogram 13f may be displayed in the Filtering Rule box. Histogram 13f may illustrate the number of defects for different values of the element and operator. In this manner, the user may be presented with information about the defects while building the rule such that the user may tailor the rule to efficiently filter the defects.

As further shown in FIG. 6, Defects Flow box 12 also includes Grouping Rule section 16. The Grouping Rule section allows the user to select which characteristics of the background and/or the defect are to be used for grouping or sorting of the defects. For example, as shown in Grouping Rule section 16, the user may select one or more background features or Context Features 18 for grouping. As shown in FIG. 6, the Context Features may include brightness, roughness, and pattern although the Context Features that are available to the user may include any other background features known in the art. In addition, although all three Context Features are shown to be selected in FIG. 6, it is to be understood that the user may select fewer than all of the available Context Features, any combination of the available Context Features, or none of the available Context Features.

The user may also or alternatively select one or more Defect Features 20 to be used for grouping of the defects. As shown in FIG. 6, the Defect Features may include size, shape, brightness, contrast, and background. However, the Defect Features that are available to the user may include fewer than all of these features. In addition, the Defect Features that are available to the user may include any other appropriate feature(s) of defects that may be used for grouping. As further shown in FIG. 6, the user may select none of the Defect Features for grouping of the defects. In particular, since the Defect Features may not necessarily be useful for grouping of defects detected in the PWQ-type methods described herein, for the methods described herein, the user may not select any of the Defect Features. However, the user may alternatively select one or more of the Defect Features to be used alone for grouping of the defects or to be used in combination with the Context Features for grouping.

The Grouping Rule Section also includes Number of Groups option 22. The user may select or alter the number of groups into which the defects are sorted using the Number of Groups option. In this example, the user may type a number of groups into the box, click the arrows next to the box until the selected number appears, or move the arrow along the scale until the selected number appears in the box. The number of groups that are selected will affect how finely the defect and/or context features are divided among the groups. Therefore, a larger number of groups will result in fewer and more similar defects assigned to each group. It is noted that the number of groups may not be specified by the user. Instead, the algorithm can automatically determine an appropriate number of groups.

Defects Flow box 12 also includes Sampling section 24 as shown in FIG. 6. The Sampling section includes Number of Defects for Review option 26, in which the user can select a total number of defects for review. Review of the defects may be performed using any appropriate defect review tool known in the art such as a SEM tool. The Sampling Section also includes Defect Priorities to Sample option 28, in which the user can select individual defect priorities that should be reviewed. As shown in FIG. 6, the defect priorities may be selected for review individually. However, the defect priorities may be selected in any manner known in the art. In addition, the Sampling section includes Defect Classes to Sample option 30, in which the user can select individual defect classes that should be reviewed. The defect classes may be selected for review individually as shown in FIG. 6 or in any other manner known in the art. In addition, an automatic sampling algorithm may be used to select defects for sampling using background and priority information. In some embodiments, a list of sample sites to visit and/or measure during review may be created based on the locations of the defects in the modulated die(s). These locations may be correlated to the location within the reticle such that the locations can be found automatically by the review tool.

As further shown in FIG. 6, the Defects Flow box also includes a number of buttons 32, which the user can select to apply the filtering, grouping, and sampling operations to the defect data. The user can apply these operations in any order. However, typically, a user may choose to filter the defects before grouping them, and to group the defects before sampling them for review. In this manner, the results of the background binning will be combined with the results of prioritized filtering so that the user can view sampled defects by a combination of the background and priority. In addition, the filtering and grouping operations can be performed iteratively rather than by fixed binning operations.

The remaining boxes shown in the screenshot of FIG. 6 can be used to display the results of the filtering, grouping, and/or sampling operations. However, these boxes may also be used to further work with the defects. For example, the user interface shown in FIG. 6 includes Defect Runs and Classes box 34, in which a stacked color bar chart is illustrated showing the results of the filtering and grouping operations. The stacked color bar chart can be used as a mechanism for illustrating and working with defect groups and priority together. Each bar represents a group of defects. Color indicates defect priorities. Although such a chart may advantageously illustrate a substantial amount of information about the defects in a relatively easy-to-comprehend manner, it is to be understood that any method or graphical structure may be used to illustrate the results of the filtering and/or grouping operations.

Figure 6B:
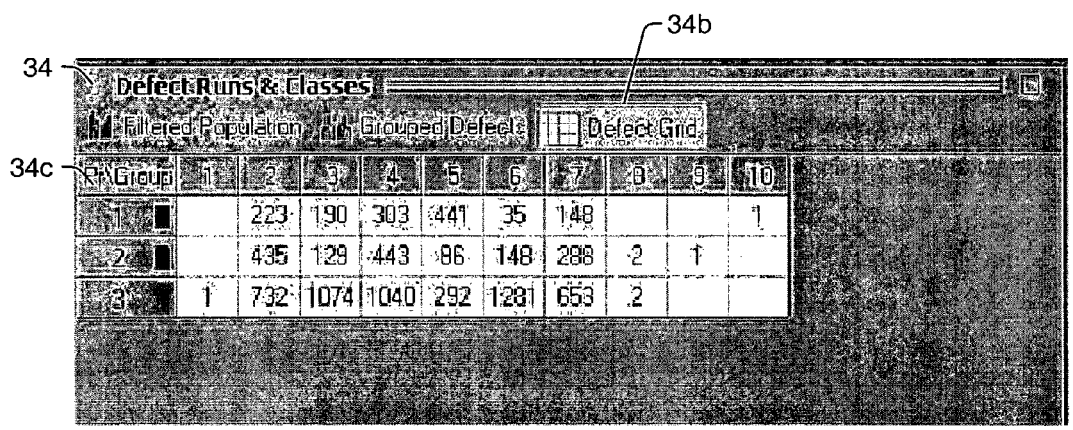

For example, the bar chart illustrated in FIG. 6 was displayed since the Grouped Defects option 34a was selected. However, if the Filtered Population and Defect Grid options are selected, different graphics will be displayed. For example, FIG. 6b illustrates another manner in which the results of filtering and grouping can be displayed when Defect Grid option 34b is selected. As shown in FIG. 6b, the Defect Runs and Classes box 34 may include grid 34c that illustrates the number of defects that were found as a function of priority and group. Although a certain number of priorities and groups are illustrated in FIG. 6b, obviously the number of priorities and groups will vary depending on the parameters used for filtering and grouping.

Figure 6C:
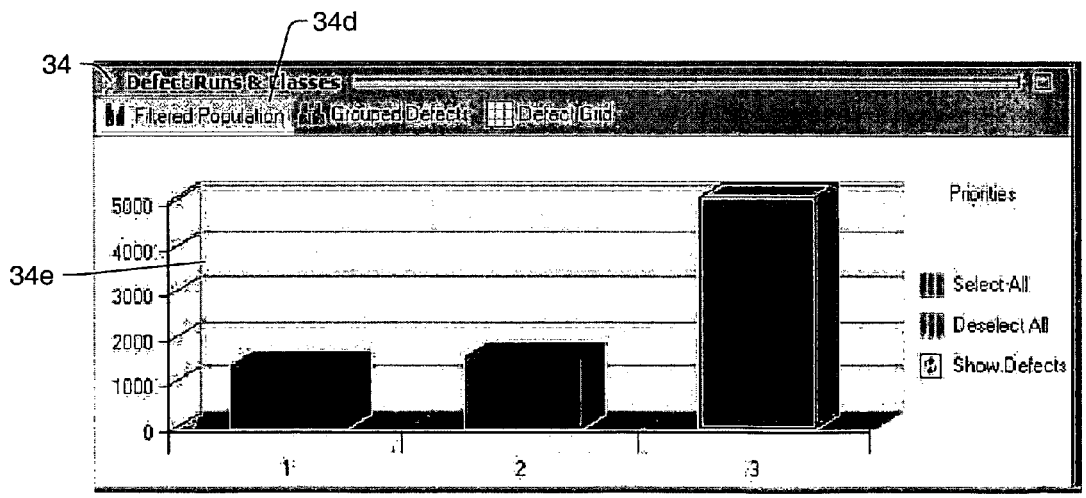

FIG. 6c illustrates a different manner in which the results of filtering and grouping can be displayed when Filtered Population option 34d is selected. As shown in FIG. 6c, the number of defects that were found as a function of priority are illustrated in bar chart 34e. However, it is to be understood that the number of defects as a function of priority may be illustrated in any other manner known in the art. In addition, although three different priorities are illustrated in FIG. 6c, it is to be understood that the number of priorities will vary depending on the parameters used for filtering.

The user interface shown in FIG. 6 may also include Available Defects box 36. The available defects box may illustrate verification defects. For example, the available defects box may illustrate the results from filtering, grouping, and retrieving. All defects which are not classified or not in classified defects folders can be displayed in an area. As shown in FIG. 6, the Available Defects box may illustrate images of the defects. Alternatively, the Available Defects box may provide information about the results using any suitable method known in the art. In addition, the user may perform one or more functions on the available defects using the Available Defects box.

The user interface may illustrate results of filtering and grouping graphically as described above and with images of defects selected for sampling. For example, as shown in Sample Defects box 38, the user interface may illustrate a folder into which defects were classified. In addition, if defects were assigned to the folders, representative defect images may be illustrated on the front of the folders. The user may perform a number of functions on the defect images shown in the Sample Defects box. For example, the user may select one of the folders into which defects were assigned. Selecting one of the folders may result in illustration of the defect images in the selected folder in box 40 below the illustration of the different folders. As shown in box 40, the defect images may also be illustrated with a number. The number may indicate the priority assigned to each defect image.

The user can move defects from one folder into another to change defect classification. The user can also perform un-classification by moving defects into the Available Defect Gallery. The user can add folders, delete the folders and rename the folders. Deleting a folder will un-classify all defects in that folder. The first folder, called Defects-to-ignore, on the left is a folder for all defects that are excluded from filtering, grouping and sampling. One or more such folders can exist. Moving defects into classified folders can be achieved, but not limited by, selecting followed by dragging and dropping the defects into the folders, or by selecting followed by clicking a button, like the Defects-to-ignore button. Although one manner of illustrating the sample images to a user is illustrated in FIG. 6, it is to be understood that any other manner of illustrating sample images may be used in the user interface and methods described herein.

Figure 6D:
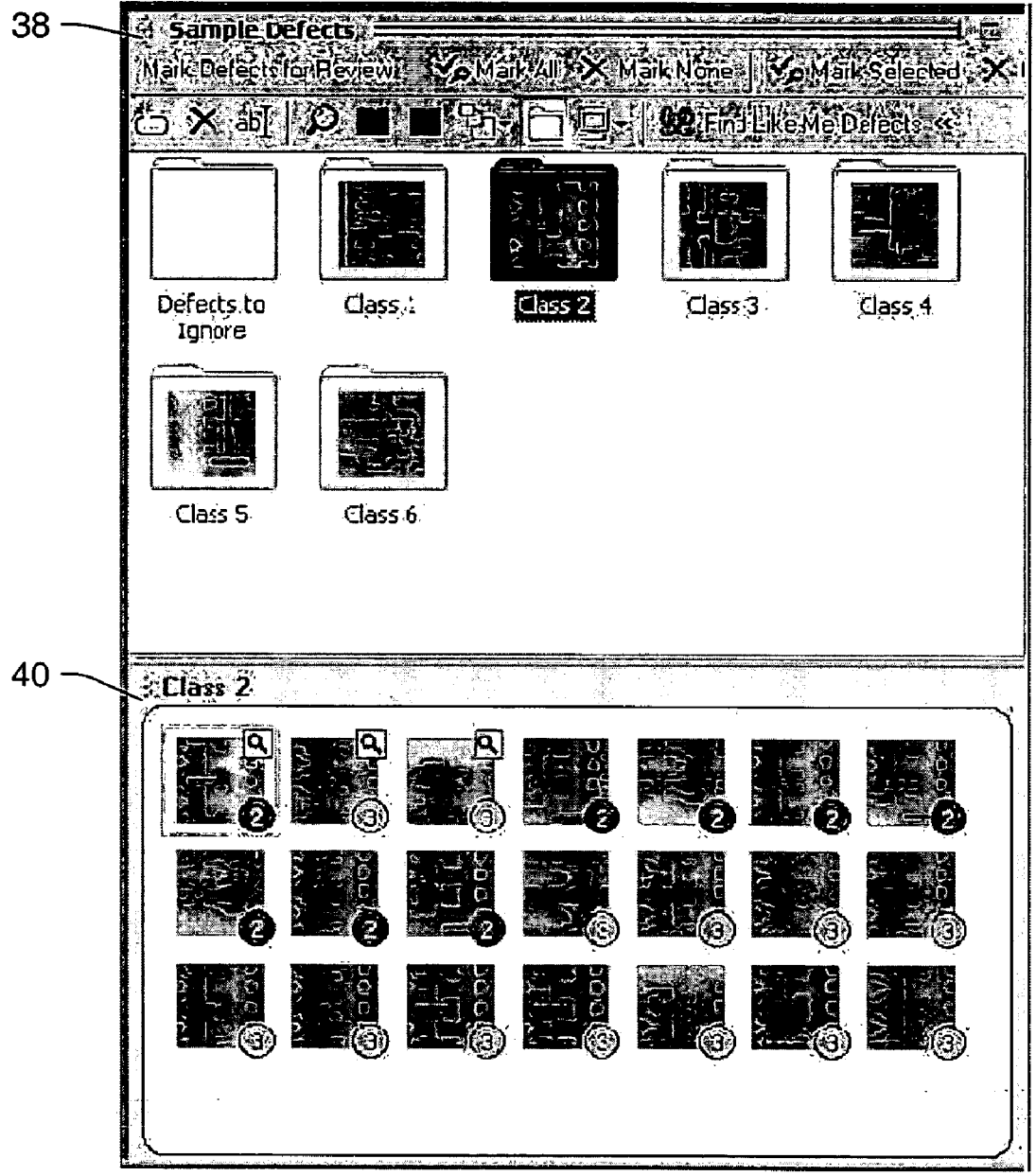

FIG. 6*d* illustrates another example of Sample Defects box 38. As shown in Sample Defect box 38 of FIG. 6*d*, the folder for Class 2 of the defects has been selected resulting in illustration of the defect images in the Class 2 folder in box 40 below the illustration of the different folders. Sampling can be performed either automatically or manually. By clicking the Apply Sampling button of buttons 32 shown in FIG. 6, the defects in classified folders are sampled according to the criteria set for sampling. The user can also select one or more defects in classified folders and mark them as sampled defects by clicking Mark Selected or Mark All, as shown in FIG. 6*d*. All sampled defects may be tagged with a marker. As further shown in FIG. 6*d*, the user can turn off the sample status for one or more defects by using the button, Unmark Selected or Unmark All.

The sample images may also be illustrated to the user in other manners. For example, the user interface may be configured to display any of the defects or just the sample images intermittently with reference images corresponding to the defect images. In this manner, the images may appear to flash in the user interface repeatedly one after the other. Such "flashing" of the images may allow the user to gain additional understanding of the differences between the images. In a similar manner, sample images of differently modulated dies may be flashed in the user interface, which may aid in user understanding of trends of the defects.

It is also noted that although the user interface is shown to include four different boxes in FIG. 6, it is to be understood that the user interface may include fewer than four information boxes or more than four information boxes. In general, the amount and organization of the information shown in the user interface may be designed to present the maximum amount of information to a user in the most manageable and easy-to-comprehend manner possible.

The user interfaces described herein provide a number of advantages in comparison to other currently used user interfaces for processing inspection results. Particularly, as described further above, the user interface provides pre-filtering capability, which may be performed based on priority and/or rules. The parameters of pre-filtering may be selected by a user as described further above. In addition, the background characteristic(s) that are used for grouping may also be selected as described herein. The background characteristic(s) may also be used with other defect attributes for grouping as described above. Furthermore, the user interface can be used to perform iterative grouping rather than fixed binning. An automatic sampling algorithm may also be used with the background grouping and priority filtering results. The functionality of the user interface may also be expanded, for example, to create a list of sample sites to visit and/or measure based on the locations of modulated die and then to make a "fake" result to be used.

Figure 7:
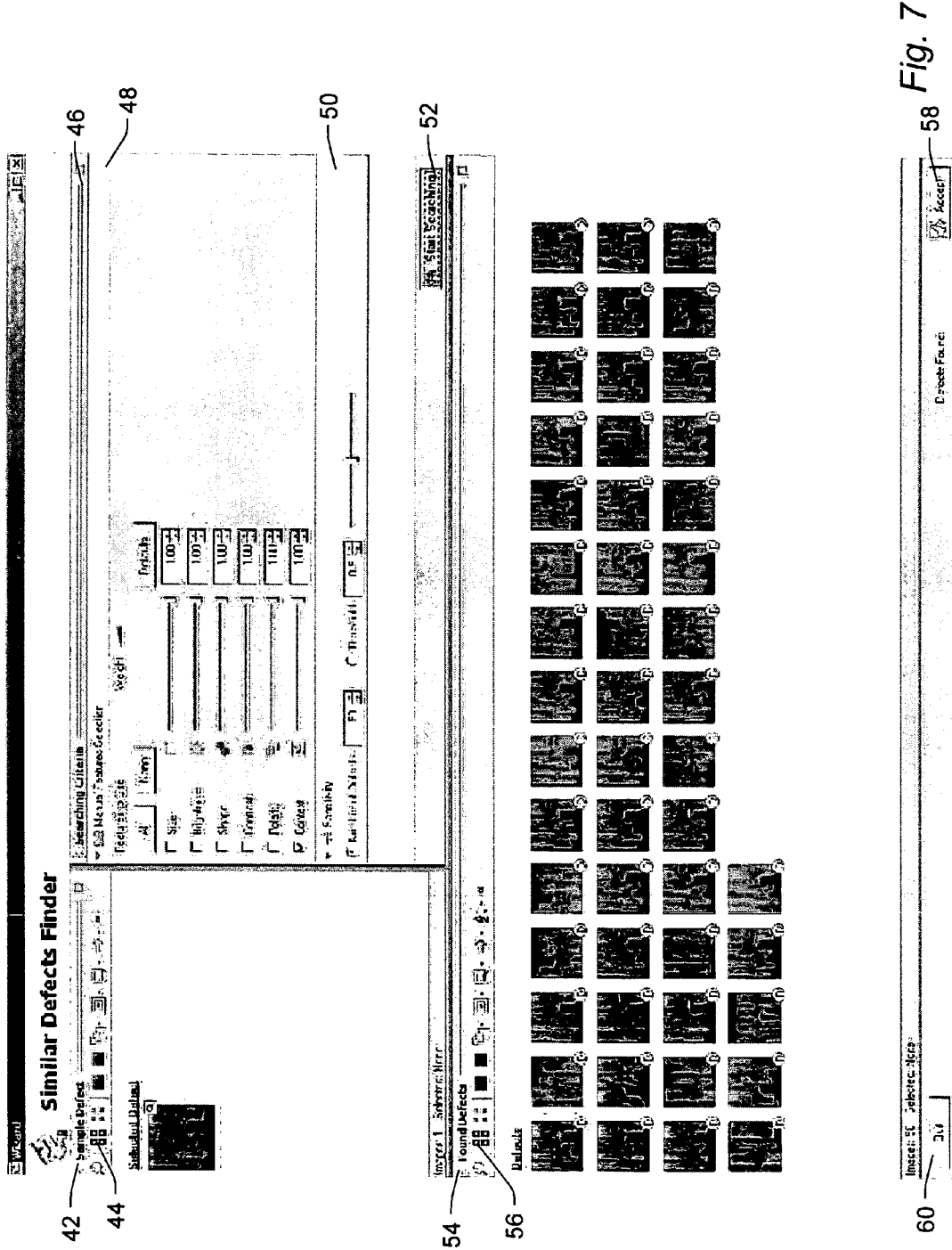

As interesting defects are found, the user can also use a different user interface to see other examples of defects that are similar to the interesting defects using a defect retrieving feature called "Defects Like Me." The user can also use this feature to remove groups of irrelevant defects in order to quickly traverse through the large number of defects. One example of a user interface that can be used to illustrate defects that are similar is shown in FIG. 7. As shown in FIG. 7, the user interface includes Sample Defect box 42, which illustrates the defect that is selected by the user. The user may select this defect from the defects illustrated in another user interface such as that shown in FIG. 6. As also shown in FIG. 7, the user may perform one or more functions on the image of the selected defect using icons 44.

The user interface also includes Searching Criteria box 46, in which the user can select one or more parameters for searching for defects that are similar to the selected defect. In particular, Searching Criteria box 46 includes Manual Features Selection section 48. In the Manual Features Selection section, the user can select one or more features of the defects to use for searching for similar defects. As shown in FIG. 7, the features that can be selected include size, brightness, shape, contrast, polarity, and context. However, it is to be understood that the features which are available for selection may include any appropriate features known in the art.

As shown in Manual Features Selection section 48, the user may also select all of the features or none of the features by clicking on the appropriate button. Alternatively, the user may manually select individual features by clicking on the boxes next to the feature name. Although only the context feature is shown to be selected in FIG. 7, it is to be understood that any of the other features may alternatively be selected or a combination of features may be selected. As described above, the context or background of the defects may be advantageously used to group defects since the features of the defects themselves may actually vary greatly from one modulated die to another. Therefore, the selected context feature may frequently be used to search for similar defects.

As further shown in FIG. 7, a weight may be assigned to each of the features to be used for searching for similar defects. The weight assigned to each feature may be a default weight assigned automatically or upon selection of the appropriate button. Although each of the default weights are shown to be the same, it is to be understood that the default weights for individual features may vary. The user may assign different weights to individual features in a number of different manners. For example, the user may type a number for the weight into the box, click the arrows next to the box until the selected weight appears, or move the arrow along the scale until the selected weight appears in the box.

As shown in FIG. 7, Searching Criteria box 46 also includes Sensitivity section 50, in which the user may select the sensitivity with which defects are to be searched. The sensitivity may be selected in different ways. For example, as shown in FIG. 7, the sensitivity may be defined by the number of defects to which the search results are limited. In other words, the number of defects shown in Sensitivity section 50 may indicate to the computer-implemented method that the searching results are to be limited to 50 defects (or some other number of defects) that are most like the selected defect. Alternatively, the user may define the sensitivity of the search by assigning a threshold to the features that are selected for the search. Although only one threshold is shown in FIG. 7, it is to be understood that the number of threshold options that are shown in FIG. 7 may vary depending on the number of features that are selected for searching.

Searching Criteria box 46 also includes Start Searching button 52 which the user can click once the appropriate choices have been made in the Searching Criteria box. During or after searching, images of the defects that are determined to be like the selected defect based on the searching criteria may be illustrated in Found Defects section 54 of the user interface. As shown in FIG. 7, the user may perform a number of different functions on the defect images using icons 56. In addition, the user may select to accept the found defects using Accept button 58. Alternatively, the user may decide to quit the "Defects Like Me" function using Quit button 60.

It is noted that although the user interface is shown to include three different boxes in FIG. 7, it is to be understood that the user interface may include fewer than three information boxes or more than three information boxes. In general, the amount and organization of the information shown in the user interface may be designed to present the maximum amount of information to a user in the most manageable and easy-to-comprehend manner possible.

In additional embodiments, the methods described herein may include altering the design pattern on the reticle based on the results of the defect detection and/or sorting methods described herein. In particular, the results of the methods described herein may be used to determine if the reticle passes qualification standards for the reticle. If the reticle does not pass qualification, then the reticle design pattern may be altered. Preferably, the reticle design pattern is altered such that fewer defects in the design pattern will be produced in the design pattern printed on the wafer. A new reticle may then be fabricated with the altered design pattern. Alternatively, in some instances, the reticle may be physically altered to alter the design pattern on the reticle. Physically altering the reticle may be performed using any repair process known in the art such as focused ion beam repair processes.

In another embodiment, the methods described herein may include generating a different design pattern for the reticle based on the results of the defect detection and/or sorting methods described herein. In particular, a new design pattern may be generated if the design pattern that was inspected was found to have a substantially large amount of defects, a relatively large number of defects that cannot be fixed, and/or defects that cannot be fixed and will cause fatal flaws in the design pattern that will be printed on the wafer. In yet another embodiment, the results of the methods described herein may be fed forward to the design process of other reticles. In particular, the results of the methods described herein may be used to design RET features in other reticles.

Some embodiments of the method may include determining a process window of the reticle. For example, it may be determined if some smaller range of the value of the lithographic variable that was examined can be used to adequately reproduce the design pattern on wafers. In this manner, the reticle may be qualified for use with a smaller than normal process window. The degree to which the process window can be narrowed in an acceptable manner will vary depending on, for example, the drift in the lithographic variable that can be expected for lithography systems that will use the reticle. In this manner, a defective reticle design pattern may be used without fixing the defects in the reticle design pattern.

Program instructions implementing methods such as those described herein may be transmitted over or stored on the carrier medium. The carrier medium may be a transmission medium such as a wire, cable, or wireless transmission link, or a signal traveling along such a wire, cable, or link. The carrier medium may also be a storage medium such as a read-only memory, a random access memory, a magnetic or optical disk, or a magnetic tape.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

The processor may take various forms, including a personal computer system, mainframe computer system, workstation, network appliance, Internet appliance, personal digital assistant ("PDA"), television system or other device. In general, the term "computer system" may be broadly defined to encompass any device having one or more processors, which executes instructions from a memory medium. In addition, the processor may include a processor as described in the patent applications incorporated by reference above, which are particularly suitable for handling a relatively large amount of image data substantially simultaneously.

Figure 8:
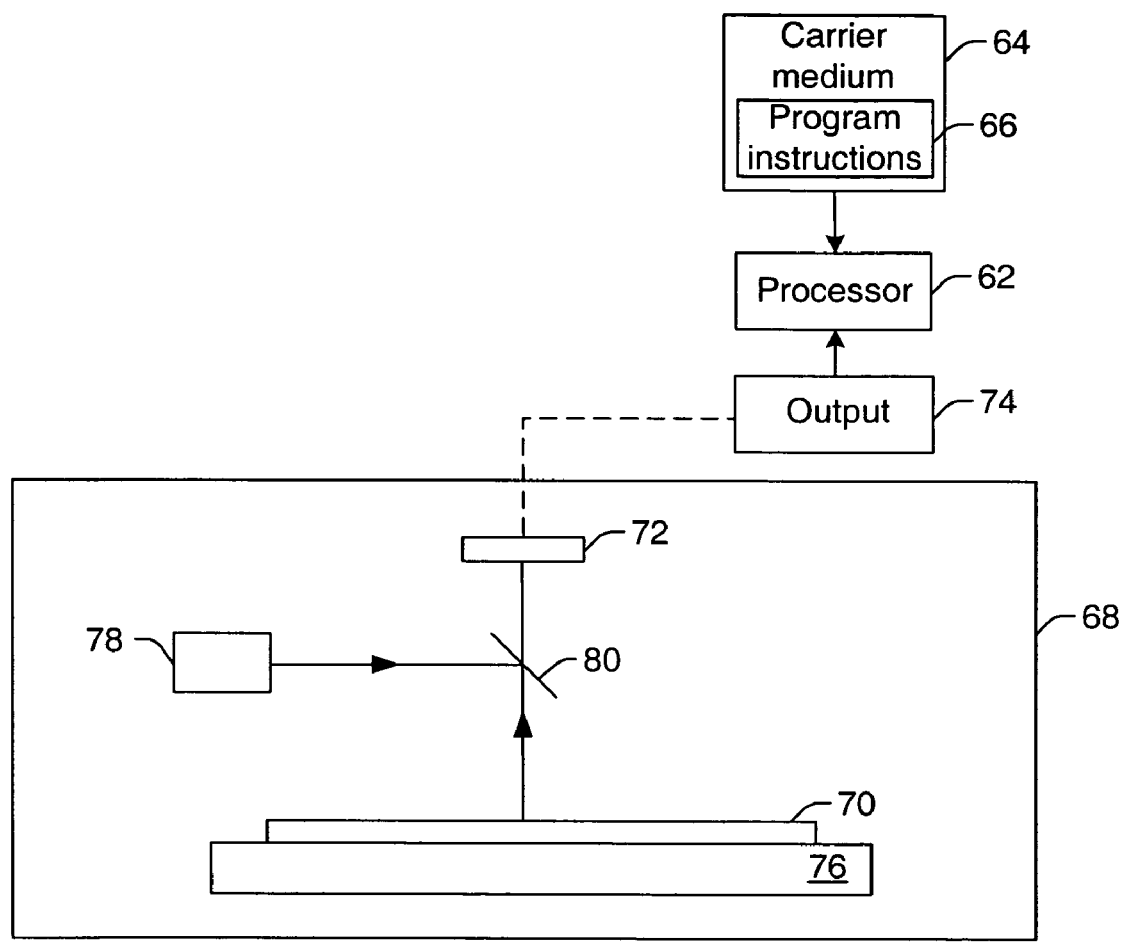
FIG. 8 is a schematic diagram illustrating a side view of one embodiment of a system that can be used to perform one or more of the computer-implemented methods described herein.

FIG. 8 illustrates one embodiment of a system configured to perform one or more of the computer-implemented methods described herein for detecting and/or sorting defects. The system shown in FIG. 8 is configured to inspect a wafer. Although the system is shown in FIG. 8 to be an optical based imaging system, it is to be understood that the system shown in FIG. 8 may be configured to image the wafer in a different way. For example, the system may be configured to inspect a wafer by imaging the wafer with electron beams (i.e., an electron beam based imaging system or SEM).

The system includes processor 62. The processor may include any suitable processor known in the art. For example, the processor may be an image computer or a parallel processor. In addition, the processor may be configured as described above. The system also includes carrier medium 64. The carrier medium may be configured as described above. For example, carrier medium 64 includes program instructions 66, which are executable on processor 62. The program instructions may be executable for performing any of the embodiments of the methods described above. The program instructions may be further configured as described above.

In some embodiments, the system may also include inspection and/or review tool 68. Tool 68 may be configured to image wafer 70 and to generate image data for the wafer that contains information about the design pattern printed on the wafer by a reticle. Tool 68 may be coupled to processor 62. For example, one or more components of tool 68 may be coupled to processor 62 by a transmission medium (not shown). The transmission medium may include "wired" and "wireless" portions. In another example, detector 72 of tool 68 may be configured to generate output 74. The output may be transmitted across a transmission medium from detector 72 to processor 62. In some embodiments, the output may also be transmitted through one or more electronic components coupled between the detector and the processor. Therefore, output 74 is transmitted from the tool to the processor, and program instructions 66 may be executable on the processor to detect and/or sort defects on the wafer as described herein using the image data included in output 74. Program instructions 66 may be further executable on the processor to perform other functions described herein (e.g., "Defects Like Me" searching, sorting defects by priority, selecting defects for sampling, etc.).

Inspection and/or review tool 68 may be configured to generate images of the wafer using any technique known in the art. In addition, the tool includes stage 76 upon which wafer 70 may be disposed during imaging or measurements. The stage may include any suitable mechanical or robotic assembly known in the art. The tool also includes light source 78. Light source 78 may include any appropriate light source known in the art. In addition, the tool may include beam splitter 80, which is configured to direct light from light source 78 onto wafer 70 at angles that are approximately normal to an upper surface of wafer 70. The beam splitter may include any suitable beam splitter known in the art. The tool further includes detector 72, which is configured to detect light transmitted by beam splitter 80. The detector is also configured to generate output 74. The detector may include any suitable detector known in the art.

Although one general configuration of the inspection and/or review tool is shown in FIG. 8, it is to be understood that the tool may have any suitable configuration known in the art. For example, the tool may be configured to perform a single channel imaging technique as shown in FIG. 8. Alternatively, the tool may be configured to perform a multiple channel imaging technique. In addition, the optical tool may be replaced with an e-beam inspection tool such as a CD SEM and the eS25 and eS30 systems, which are commercially available from KLA-Tencor. Such a tool may be coupled to the processor as described above.

Figure 9:
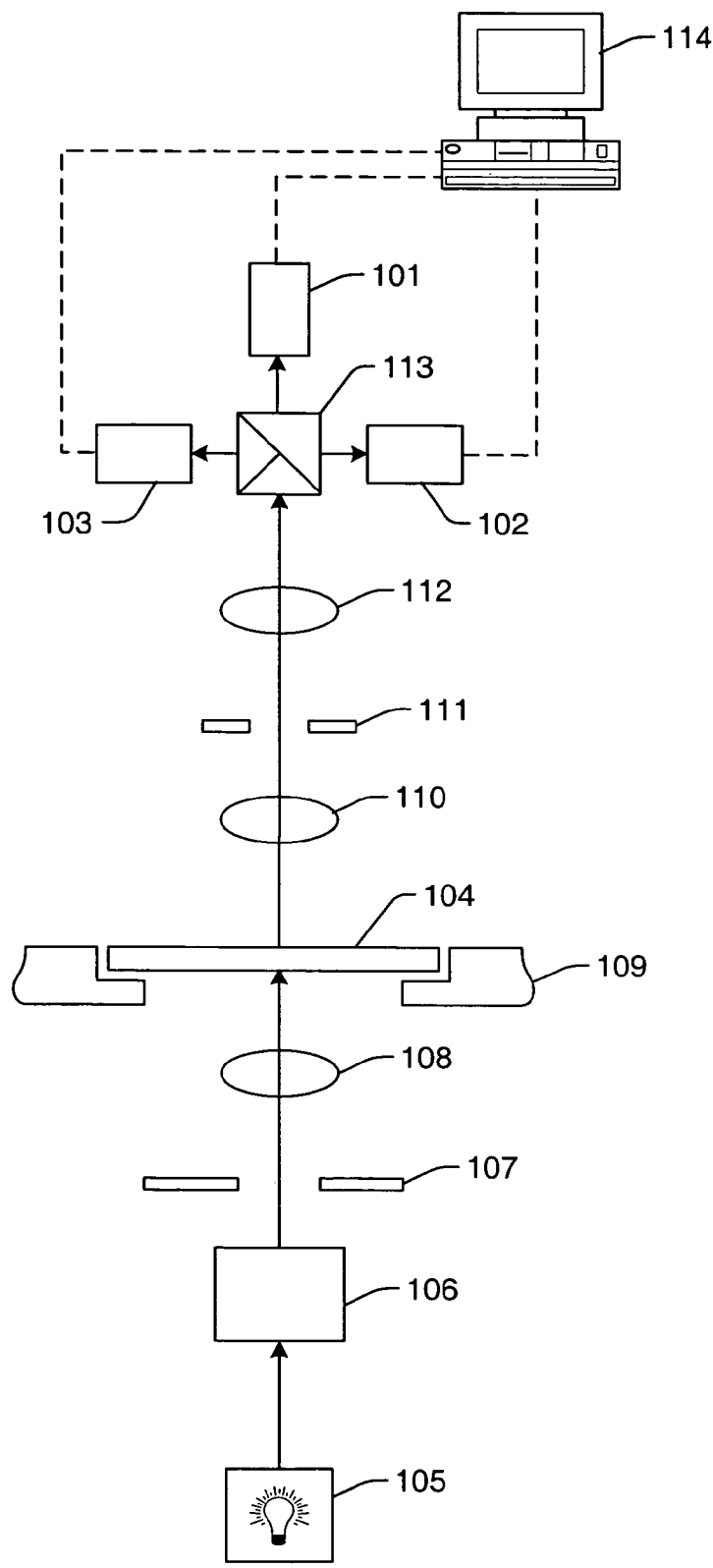
FIG. 9 is schematic diagram illustrating a side view of an apparatus that can be used to acquire aerial images of a design pattern of a reticle.

In another embodiment, the computer-implemented methods described above may be performed using aerial images. For example, the methods described herein may be implemented using an aerial image measurement system (AIMS) technique, which may be better understood by reference to FIG. 9. In FIG. 9, a system is shown having three detectors, i.e., detectors 101, 102 and 103. Each of these detectors may preferably be set at a different focal position. For example, detector 101 could be at zero defocus, detector 102 could be at +0.2 defocus, and detector 103 could be at −0.2 defocus. Of course, these levels of defocus are only examples. Any suitable range or levels of defocus could be used, and such levels could be optimized empirically. It is not necessary to use a detector having zero defocus, for example, and all of the detectors could be set at varying levels of positive defocus, or at mixed levels of positive and negative defocus.

Sample 104 is preferably a mask or reticle. As sample 104 is exposed to illumination source 105, an aerial image is detected at the three detectors. Because of their different focal positions, the aerial images at each detector will have different levels of defocus. Images having varying levels of defocus may be compared and analyzed using any of the techniques previously set forth herein. In a preferred embodiment, signals taken from a first detector, such as detector 101, are compared to signals taken from a second detector, such as detector 102, continuously as sample 104 is inspected. This is only one example, of course, and images from any pairs of detectors could be compared. Alternatively, comparisons could be made between detectors and mathematical combinations of other detectors (such as a pixel by pixel average between a pair of detectors, or a difference between another pair of detectors). Preferably, the levels of defocus and/or the types of comparisons between the signals from the various detectors (or combinations thereof) are selected to provide the user with information regarding RET defects and the appearance of such defects across a process window.

In the embodiment shown in FIG. 9, it is possible to simultaneously perform a conventional inspection and a process window qualification. The purpose and methodology of the process window qualification (to find RET defects and the like) has already been described herein. The purpose of the conventional inspection is to find other types of defects, such as defects resulting from reticle manufacturing errors and/or from contaminants on the reticle. A method of such a conventional inspection is described in U.S. Pat. No. 6,268,093 to Kenan et al., which is incorporated by reference as if fully set forth herein. Other suitable methods of performing such inspections are described in more detail in a commonly assigned co-pending application by Stokowski et al. having U.S. Ser. No. 10/679,617, filed Oct. 6, 2003, which is incorporated by reference herein in its entirety and for all purposes. Such suitable methods include, without limitation, a die-to-database inspection in which the reticle is inspected by comparison against a rendered database from which the reticle was created.

In a preferred embodiment, the conventional inspection is done by comparing signals from the same detector taken at nominally identical portions of different dies. This inspection process works well for multi-die reticles. The process window qualification is performed substantially simultaneously, and may be achieved as already described herein by comparing images at varying levels of defocus for each die. So the conventional inspection might be achieved by comparing images from a first die on sample 104 to images of a second die on sample 104, wherein each image is detected using detector 101. At substantially the same time as the images of each such die are collected for purposes of the conventional inspection, for each such die an image from detector 101 and/or detector 102 or detector 103, is also compared to an image of that same die taken at a different focal position (for example from another of detectors 101, 102 and/or 103, or any mathematical combination thereon). Thus, the conventional inspection and process window qualification may be performed substantially simultaneously.

If desired, the processing of the data from the conventional inspection and from the process window qualification could be performed on the same computer by using parallel processing. A suitable architecture and methodology are described in more detail in a commonly assigned co-pending application by Goldberg et al. having U.S. Ser. No. 09/449,022, filed Nov. 24, 1999, which is incorporated by reference herein in its entirety and for all purposes.

In yet another embodiment of the invention, and in accordance with the above description of the example shown in FIG. 9, a single die reticle could be provided as sample 104, and only a process window qualification may be performed using the apparatus shown in FIG. 9. Such a technique may be desirable for all types of reticles, and may be particularly desirable for single die reticles. This is because the apparatus shown in FIG. 9 is in many ways inferior to other types of inspection systems, such as the 3XX and 5XX series commercially available from KLA-Tencor Corporation. Thus, it may be desirable to find conventional defects using the KLA-Tencor tools, and then inspect the same reticle again in an aerial image mode to locate RET defects by varying the process window. As mentioned above, this may be particularly desirable where sample 104 is a single die reticle. This avoids the need to render the design database in a mode suitable for comparison against the aerial image. Instead, the aerial image is used only for purposes of finding RET defects, and the conventional inspection is done using a more accurate tool which can directly compare the actual image of the reticle to the rendered database (including the OPC features present therein).

Of course, if a suitably rendered database is available for comparison against the AIMS image (rendered using the techniques described, for example, in the application by Stokowski et al., as mentioned above), a die-to-database inspection could be done using an AIMS tool such as that shown in FIG. 9. In such a case, it is possible to also do the inspection for RET defects by using a comparison against the rendered database. For example, the conventional inspection could be performed by comparing images from a detector at zero defocus to images rendered from the database, also at zero defocus. The RET defects could then be found by comparing the images from one or more detectors, at varying levels of defocus, against the rendered database at zero defocus. Or the database could also be, through simulation, rendered in a manner that is consistent with a given level of defocus. In either situation, the methods described herein could be applied to find RET defects.

The present invention is not limited to just finding RET defects by varying the level of defocus. As noted above, varying sigma and/or the numerical aperture (NA) of the system are also relevant to the process window. Varying these parameters can, therefore, be used to find RET defects. One method of achieving this is to take an image obtained using an inspection under a first set of conditions (i.e., a first set of sigma, NA and defocus), then take an image of the same reticle under a second set of conditions (i.e, varying one or more of the NA, sigma and defocus), and compare the resulting images. Such a method can be implemented, using an apparatus such as that shown in FIG. 9, simply by storing data taken from a first inspection of a reticle under a first set of conditions, varying parameters such as sigma, NA and/or defocus on the apparatus, and then re-inspecting the same reticle with the new parameter settings in place. The images are aligned prior to comparison. The stored data could be taken from inspection of an entire reticle (and stored on an optical disk or other media having suitable storage space), or could be taken across just a portion of the reticle (such as one or more swaths). If only a portion of the reticle inspection data is stored, storage might be appropriately handled in a memory buffer or the like. In some embodiments, the stored data may represent a "reference reticle field," or an aerial image of the reticle that would be produced at the best known process conditions, which may be stored such that it can be later used for transient repeating defect detection and/or non-transient defect detection.

In another embodiment, stored data could be taken from inspection of an entire die or just a portion of the die. In one such embodiment, the die or the portion of the die may correspond to a design pattern that is formed on the wafer using a reference value of a lithographic variable, which in some embodiments may be the best known conditions. In this manner, the stored data may represent a "reference die." In alternative embodiments, the stored data may be a simulated image. For example, the simulated image may be an image that would be printed on the wafer at the reference member value. In one embodiment, the simulated image may be generated from reticle design data. The reticle design data may be altered based on the reference value to generate a simulated aerial image of the reticle. In a different embodiment, the simulated image may be generated from an aerial image of the reticle that is acquired by reticle inspection. The simulated aerial image or the acquired aerial image may be altered using a resist model to generate an image of the reticle that would be printed on the wafer at the reference value.

The stored data may be compared to other die or portions of die on the wafer to determine a presence of defects on the wafer. In some embodiments, the die that are compared to the stored data may be printed at different conditions (i.e., not the reference value). As such, the stored data may be used to determine a presence of transient repeating defects in the die or the portions of the die on the wafer. Alternatively, the die that are compared to the stored data may be printed at the same conditions as the stored data (i.e., the reference value). Therefore, the stored data may be used to determine a presence of non-transient defects in the die or the portions of the die on the wafer.

As shown in FIG. 9, the system may include a number of other components including, but not limited to, homogenizer 106, aperture 107, condenser lens 108, stage 109, objective lens 110, aperture 111, lens 112, beamsplitter 113, and processor or computer 114. The components may be configured as described in more detail in a commonly assigned co-pending application by Stokowski et al. having U.S. Ser. No. 10/679,617, filed Oct. 6, 2003. These components may be altered to provide varying parameters such as sigma, NA, the type of illumination, and the shape of the beam. For example, aperture 107 may be altered to change sigma, the NA, the type of illumination, and the shape of the beam.

In a preferred embodiment, rather than directly comparing raw data from each detector (and/or from a rendered database), it may be desirable to preprocess the data prior to comparison, as described in U.S. Patent Application Publication No. US2004/0091142 to Peterson et al., which is incorporated by reference as if fully set forth herein.

In another preferred embodiment, the data taken from inspection by any method described herein (e.g., inspection using aerial images, inspection of images printed on a wafer, inspection of simulated images in accordance with DRC techniques, etc.) may be used to flag regions of a reticle or wafer for review. The defects may be selected for review as described above. The coordinates for such review could be stored by the inspection apparatus and passed to a review tool (or performed on a review tool integrated into the inspection apparatus). In one preferred embodiment, the review tool is an aerial image review tool of the type commercially available from Carl Zeiss, Inc., Germany. Potential RET defect locations on a reticle are identified, and the coordinates are passed to the Zeiss tool. Each such potential defect (or a sample statistically selected from a group of such defects) is then reviewed at varying levels of defocus (or other optical conditions, such as sigma or NA) to further study the possible defect and its potential significance.

It is to be noted that the above methods that use aerial images may also be performed in a similar manner using simulated images (e.g., images acquired using DRC techniques or ORC techniques).

Further modifications and alternative embodiments of various aspects of the invention may be apparent to those skilled in the art in view of this description. For example, computer-implemented methods for detecting and/or sorting defects in a design pattern of a reticle are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for sorting defects in a design pattern of a reticle, comprising:

searching for defects of interest in inspection data using priority information and defect attributes associated with individual defects in combination with one or more characteristics of a region proximate the individual defects and one or more characteristics of the individual defects, wherein the inspection data is generated by comparing images of the reticle to each other to detect the individual defects in the design pattern of the reticle, wherein the images that are compared to each other are generated for different values of a lithographic variable, wherein the images comprise at least one reference image and at least one modulated image, and wherein the priority information is derived from a relationship between the individual defects and their corresponding modulation levels of the lithographic variable; and assigning one or more identifiers to the defects of interest.

2. The method of claim 1, wherein the defect attributes comprise inspection parameter information, simple defect information comprising location, size and intensity magnitude, and a relationship among individual defects.

3. The method of claim 1, further comprising filtering the individual defects based on the priority information and the defect attributes.

4. The method of claim 3, wherein criteria for the filtering can be selected by a user.

5. The method of claim 1, wherein the one or more characteristics of the region proximate the individual defects and on the individual defects are derived from the at least one reference image and the at least one modulated image, respectively.

6. The method of claim 1, wherein the one or more characteristics of the region proximate the individual defects are selected by a user.

7. The method of claim 1, further comprising grouping the defects of interest based on the one or more characteristics of the region proximate the individual defects.

8. The method of claim 7, further comprising analyzing one or more characteristics of the region proximate one or more of the individual defects in a group to determine if the group is an irrelevant defect group.

9. The method of claim 1, further comprising grouping the defects of interest based on the one or more characteristics of the region proximate the individual defects in combination with the one or more characteristics of the defects of interest.

10. The method of claim 9, further comprising refining the grouping of the defects of interest based on similarity of the individual defects to a selected defect based on the one or more characteristics of the region proximate the individual defects or the individual defects themselves.

11. The method of claim 1, wherein the one or more identifiers comprise a defect classification.

12. The method of claim 1, wherein the one or more identifiers comprise an indicator identifying if the defects of interest are to be selected for future processing.

13. The method of claim 1, wherein the one or more identifiers comprise an indicator identifying if the defects of interest are to be selected for future processing, and wherein said assigning the one or more identifiers is performed through a sampling algorithm performed automatically based on the priority information and the one or more identifiers.

14. The method of claim 1, further comprising comparing the defects of interest to inspection data generated by design rule checking performed on design pattern data of the reticle to determine if the defects of interest correlate to design rule checking defects.

15. The method of claim 14, further comprising removing from the defects of interest the defects that do not correlate with results of the design rule checking.

16. The method of claim 1, wherein the one or more characteristics of the region comprise one or more characteristics of the region extracted from a GDS or aerial image.

17. The method of claim 1, wherein the one or more characteristics of the region comprise one or more characteristics of the region determined from a high resolution image.

18. A storage medium, comprising program instructions executable on a computer system to perform a computer-implemented method for sorting defects in a design pattern of a reticle, wherein the computer-implemented method comprises:

searching for defects of interest in inspection data using priority information and defect attributes associated with individual defects in combination with one or more characteristics of a region proximate the individual defects and one or more characteristics of the individual defects, wherein the inspection data is generated by comparing images of the reticle to each other to detect the individual defects in the design pattern of the reticle, wherein the images that are compared to each other are generated for different values of a lithographic variable, wherein the images comprise at least one reference image and at least one modulated image, and wherein the priority information is derived from a relationship between the individual defects and their corresponding modulation levels of the lithographic variable; and assigning one or more identifiers to the defects of interest.

19. A system configured to sort defects in a design pattern of a reticle, comprising:

an inspection tool configured to generate image data for a wafer that contains information about the design pattern printed on the wafer by the reticle;

a processor configured to receive the image data; and a storage medium comprising program instructions executable on the processor for performing a computer-implemented method, wherein the computer-implemented method comprises;

generating inspection data by comparing the image data to each other to detect individual defects in the design pattern of the reticle, wherein the image data that is compared to each other is generated for different values of a lithographic variable, and wherein the image data comprises at least one reference image and at least one modulated image;

searching for defects of interest in the inspection data using priority information and defect attributes associated with the individual defects in combination with one or more characteristics of a region proximate the individual defects and one or more characteristics of the individual defects, wherein the priority information is derived from a relationship between the individual defects and their corresponding modulation levels of the lithographic variable; and assigning one or more identifiers to the defects of interest.

* * * * *